US009724666B1

(12) United States Patent
Rajeev et al.

(10) Patent No.: US 9,724,666 B1
(45) Date of Patent: Aug. 8, 2017

(54) APPARATUS FOR LARGE VOLUME AMMONOTHERMAL MANUFACTURE OF GALLIUM NITRIDE CRYSTALS AND METHODS OF USE

(71) Applicant: Soraa, Inc., Fremont, CA (US)

(72) Inventors: Pakalapati Tirumala Rajeev, Santa Barbara, CA (US); Douglas W. Pocius, Santa Barbara, CA (US); Mark P. D'Evelyn, Santa Barbara, CA (US)

(73) Assignee: Soraa, Inc., Fremont, CA (US)

( * ) Notice: Subject to any disclaimer, the term of this patent is extended or adjusted under 35 U.S.C. 154(b) by 1160 days.

(21) Appl. No.: 13/656,615

(22) Filed: Oct. 19, 2012

Related U.S. Application Data

(60) Provisional application No. 61/549,893, filed on Oct. 21, 2011.

(51) Int. Cl.
*B01J 19/06* (2006.01)
*C30B 7/10* (2006.01)
*C30B 35/00* (2006.01)

(52) U.S. Cl.
CPC ............. *B01J 19/06* (2013.01); *C30B 7/10* (2013.01); *C30B 35/00* (2013.01)

(58) Field of Classification Search
CPC combination set(s) only.
See application file for complete search history.

(56) References Cited

U.S. PATENT DOCUMENTS

| 2,979,413 | A | * | 4/1961 | Ballman | C30B 29/00 117/71 |
|---|---|---|---|---|---|
| 4,019,950 | A | * | 4/1977 | Croxall | C01G 21/14 117/71 |
| 4,030,966 | A | | 6/1977 | Hornig et al. | |

(Continued)

FOREIGN PATENT DOCUMENTS

| CN | 101061570 | 10/2007 |
|---|---|---|
| JP | 2005289797 | 10/2005 |

(Continued)

OTHER PUBLICATIONS

Altoukhov et al., 'High reflectivity airgap distributed Bragg reflectors realized by wet etching of AlInN sacrificial layers', Applied Physics Letters, vol. 95, 2009, pp. 191102-1-191102-3.

(Continued)

*Primary Examiner* — Duy Deo
*Assistant Examiner* — Erin Bergner
(74) *Attorney, Agent, or Firm* — Saul Ewing LLP

(57) ABSTRACT

An apparatus to contain the reaction vessel in which gallium nitride crystals (henceforth referred to as bulk crystals) can be grown using the ammonothermal method at high pressure and temperature is disclosed. The apparatus provides adequate containment in all directions, which, for a typical cylindrical vessel, can be classified as radial and axial. Furthermore, depending on the specifics of the design parameters, the apparatus is capable of operating at a temperature up to 1,200 degrees Celsius, a pressure up to 2,000 MPa, and for whatever length of time is necessary to grow (Continued)

satisfactory bulk crystals. The radial constraint in the current disclosure is provided by using several stacked composite rings. The design of the apparatus is scalable to contain reaction volumes larger than 100 cubic centimeters.

22 Claims, 10 Drawing Sheets

(56) References Cited

U.S. PATENT DOCUMENTS

| | | |
|---|---|---|
| 4,066,868 A | 1/1978 | Witkin et al. |
| 4,350,560 A | 9/1982 | Helgeland et al. |
| 5,098,673 A | 3/1992 | Engel et al. |
| 5,169,486 A | 12/1992 | Young et al. |
| 5,474,021 A | 12/1995 | Tsuno et al. |
| 6,129,900 A | 10/2000 | Satoh et al. |
| 6,273,948 B1 | 8/2001 | Porowski et al. |
| 6,398,867 B1 | 6/2002 | D'Evelyn et al. |
| 6,406,540 B1 | 6/2002 | Harris et al. |
| 6,528,427 B2 | 3/2003 | Chebi et al. |
| 6,533,874 B1 | 3/2003 | Vaudo et al. |
| 6,596,079 B1 | 7/2003 | Vaudo et al. |
| 6,639,925 B2 | 10/2003 | Niwa et al. |
| 6,656,615 B2 | 12/2003 | Dwilinski et al. |
| 6,686,608 B1 | 2/2004 | Takahira |
| 6,764,297 B2 | 7/2004 | Godwin et al. |
| 6,765,240 B2 | 7/2004 | Tischler et al. |
| 6,784,463 B2 | 8/2004 | Camras et al. |
| 6,787,814 B2 | 9/2004 | Udagawa |
| 6,858,882 B2 | 2/2005 | Tsuda et al. |
| 6,861,130 B2 | 3/2005 | D'Evelyn et al. |
| 6,887,144 B2 | 5/2005 | D'Evelyn et al. |
| 7,001,577 B2 | 2/2006 | Zimmerman et al. |
| 7,012,279 B2 | 3/2006 | Wierer Jr. et al. |
| 7,026,756 B2 | 4/2006 | Shimizu et al. |
| 7,053,413 B2 | 5/2006 | D'Evelyn et al. |
| 7,063,741 B2 | 6/2006 | D'Evelyn et al. |
| 7,078,731 B2 | 7/2006 | D'Evelyn et al. |
| 7,098,487 B2 | 8/2006 | D'Evelyn et al. |
| 7,112,829 B2 | 9/2006 | Picard et al. |
| 7,119,372 B2 | 10/2006 | Stokes et al. |
| 7,125,453 B2 | 10/2006 | D'Evelyn et al. |
| 7,160,531 B1 | 1/2007 | Jacques et al. |
| 7,170,095 B2 | 1/2007 | Vaudo et al. |
| 7,175,704 B2 | 2/2007 | D'Evelyn et al. |
| 7,198,671 B2 | 4/2007 | Ueda |
| 7,252,712 B2 | 8/2007 | Dwilinski et al. |
| 7,279,040 B1 | 10/2007 | Wang |
| 7,285,801 B2 | 10/2007 | Eliashevich et al. |
| 7,316,746 B2 | 1/2008 | D'Evelyn et al. |
| 7,368,015 B2 | 5/2008 | D'Evelyn et al. |
| 7,381,391 B2 | 6/2008 | Spencer et al. |
| 7,420,261 B2 | 9/2008 | Dwilinski et al. |
| 7,569,206 B2 | 8/2009 | Spencer et al. |
| 7,625,446 B2 | 12/2009 | D'Evelyn et al. |
| 7,642,122 B2 | 1/2010 | Tysoe et al. |
| 7,704,324 B2 | 4/2010 | D'Evelyn et al. |
| 7,705,276 B2 | 4/2010 | Giddings et al. |
| 7,759,710 B1 | 7/2010 | Chiu et al. |
| 7,871,839 B2 | 1/2011 | Lee et al. |
| 7,976,630 B2 | 7/2011 | Poblenz et al. |
| 8,021,481 B2 | 9/2011 | D'Evelyn |
| 8,048,225 B2 | 11/2011 | Poblenz et al. |
| 8,097,081 B2 | 1/2012 | D'Evelyn |
| 8,148,801 B2 | 4/2012 | D'Evelyn |
| 8,188,504 B2 | 5/2012 | Lee |
| 8,198,643 B2 | 6/2012 | Lee et al. |
| 8,207,548 B2 | 6/2012 | Nagai |
| 8,278,656 B2 | 10/2012 | Mattmann et al. |
| 8,284,810 B1 | 10/2012 | Sharma et al. |
| 8,299,473 B1 | 10/2012 | D'Evelyn et al. |
| 8,303,710 B2 | 11/2012 | D'Evelyn |
| 8,306,081 B1 | 11/2012 | Schmidt et al. |
| 8,323,405 B2 | 12/2012 | D'Evelyn |
| 8,329,511 B2 | 12/2012 | D'Evelyn |
| 8,354,679 B1 | 1/2013 | D'Evelyn et al. |
| 8,430,958 B2 | 4/2013 | D'Evelyn |
| 8,435,347 B2 | 5/2013 | D'Evelyn et al. |
| 8,444,765 B2 | 5/2013 | D'Evelyn |
| 8,461,071 B2 | 6/2013 | D'Evelyn |
| 8,465,588 B2 | 6/2013 | Poblenz et al. |
| 8,482,104 B2 | 7/2013 | D'Evelyn et al. |
| 8,492,185 B1 | 7/2013 | D'Evelyn et al. |
| 8,729,559 B2 | 5/2014 | Krames et al. |
| 2001/0009134 A1 | 7/2001 | Kim et al. |
| 2001/0011935 A1 | 8/2001 | Lee et al. |
| 2001/0048114 A1 | 12/2001 | Morita et al. |
| 2002/0070416 A1 | 6/2002 | Morse et al. |
| 2002/0105986 A1 | 8/2002 | Yamasaki |
| 2002/0182768 A1 | 12/2002 | Morse et al. |
| 2002/0189532 A1 | 12/2002 | Motoki et al. |
| 2003/0027014 A1 | 2/2003 | Johnson et al. |
| 2003/0140845 A1* | 7/2003 | D'Evelyn ............... B01J 3/062 117/8 |
| 2003/0145784 A1 | 8/2003 | Thompson et al. |
| 2003/0164507 A1 | 9/2003 | Edmond et al. |
| 2003/0183155 A1 | 10/2003 | D'Evelyn et al. |
| 2003/0209191 A1 | 11/2003 | Purdy |
| 2003/0232512 A1 | 12/2003 | Dickinson et al. |
| 2004/0000266 A1 | 1/2004 | D'Evelyn et al. |
| 2004/0023427 A1 | 2/2004 | Chua et al. |
| 2004/0124435 A1 | 7/2004 | D'Evelyn et al. |
| 2004/0161222 A1 | 8/2004 | Niida et al. |
| 2004/0245535 A1 | 12/2004 | D'Evelyn et al. |
| 2005/0087753 A1 | 4/2005 | D'Evelyn et al. |
| 2005/0098095 A1 | 5/2005 | D'Evelyn et al. |
| 2005/0109240 A1 | 5/2005 | Maeta et al. |
| 2005/0121679 A1 | 6/2005 | Nagahama et al. |
| 2005/0128469 A1 | 6/2005 | Hall et al. |
| 2005/0152820 A1 | 7/2005 | D'Evelyn et al. |
| 2005/0167680 A1 | 8/2005 | Shei et al. |
| 2005/0205215 A1 | 9/2005 | Giddings et al. |
| 2005/0263791 A1 | 12/2005 | Yanagihara et al. |
| 2006/0021582 A1 | 2/2006 | Saito et al. |
| 2006/0032428 A1 | 2/2006 | Dwilinski et al. |
| 2006/0037529 A1 | 2/2006 | D'Evelyn et al. |
| 2006/0037530 A1 | 2/2006 | Dwilinski et al. |
| 2006/0048699 A1 | 3/2006 | D'Evelyn et al. |
| 2006/0096521 A1 | 5/2006 | D'Evelyn et al. |
| 2006/0118799 A1 | 6/2006 | D'Evelyn et al. |
| 2006/0124051 A1 | 6/2006 | Yoshioka et al. |
| 2006/0163589 A1 | 7/2006 | Fan et al. |
| 2006/0169993 A1 | 8/2006 | Fan et al. |
| 2006/0177362 A1 | 8/2006 | D'Evelyn et al. |
| 2006/0207497 A1 | 9/2006 | D'Evelyn et al. |
| 2006/0213429 A1 | 9/2006 | Motoki et al. |
| 2006/0214287 A1 | 9/2006 | Ogihara et al. |
| 2006/0255341 A1 | 11/2006 | Pinnington et al. |
| 2006/0255343 A1 | 11/2006 | Ogihara et al. |
| 2006/0288927 A1 | 12/2006 | Chodelka et al. |
| 2007/0057337 A1 | 3/2007 | Kano et al. |
| 2007/0096239 A1 | 5/2007 | Cao et al. |
| 2007/0105351 A1 | 5/2007 | Motoki et al. |
| 2007/0114569 A1 | 5/2007 | Wu et al. |
| 2007/0121690 A1 | 5/2007 | Fujii et al. |
| 2007/0131967 A1 | 6/2007 | Kawaguchi et al. |
| 2007/0141819 A1 | 6/2007 | Park et al. |
| 2007/0142204 A1 | 6/2007 | Park et al. |
| 2007/0151509 A1 | 7/2007 | Park et al. |
| 2007/0158785 A1 | 7/2007 | D'Evelyn et al. |
| 2007/0178039 A1 | 8/2007 | D'Evelyn et al. |
| 2007/0181056 A1 | 8/2007 | D'Evelyn et al. |
| 2007/0197004 A1 | 8/2007 | Dadgar et al. |
| 2007/0210074 A1 | 9/2007 | Maurer et al. |
| 2007/0215033 A1 | 9/2007 | Imaeda et al. |
| 2007/0215887 A1 | 9/2007 | D'Evelyn et al. |
| 2007/0218703 A1 | 9/2007 | Kaeding et al. |
| 2007/0228404 A1 | 10/2007 | Tran et al. |
| 2007/0252164 A1 | 11/2007 | Zhong et al. |
| 2007/0274359 A1 | 11/2007 | Takeuchi et al. |
| 2007/0290224 A1 | 12/2007 | Ogawa |
| 2008/0006831 A1 | 1/2008 | Ng |
| 2008/0023691 A1 | 1/2008 | Jang et al. |

(56) References Cited

U.S. PATENT DOCUMENTS

| | | |
|---|---|---|
| 2008/0025360 A1 | 1/2008 | Eichler et al. |
| 2008/0056984 A1 | 3/2008 | Yoshioka et al. |
| 2008/0073660 A1 | 3/2008 | Ohno et al. |
| 2008/0083741 A1 | 4/2008 | Giddings et al. |
| 2008/0083929 A1 | 4/2008 | Fan et al. |
| 2008/0083970 A1 | 4/2008 | Kamber et al. |
| 2008/0087919 A1 | 4/2008 | Tysoe et al. |
| 2008/0106212 A1 | 5/2008 | Yen et al. |
| 2008/0121906 A1 | 5/2008 | Yakushiji |
| 2008/0128752 A1 | 6/2008 | Wu |
| 2008/0156254 A1 | 7/2008 | Dwilinski et al. |
| 2008/0193363 A1 | 8/2008 | Tsuji |
| 2008/0198881 A1 | 8/2008 | Farrell et al. |
| 2008/0211416 A1 | 9/2008 | Negley et al. |
| 2008/0230765 A1 | 9/2008 | Yoon et al. |
| 2008/0272462 A1 | 11/2008 | Shimamoto et al. |
| 2008/0282978 A1 | 11/2008 | Butcher et al. |
| 2008/0285609 A1 | 11/2008 | Ohta et al. |
| 2008/0298409 A1 | 12/2008 | Yamashita et al. |
| 2009/0078955 A1 | 3/2009 | Fan et al. |
| 2009/0092536 A1 | 4/2009 | Kawabata et al. |
| 2009/0146170 A1 | 6/2009 | Zhong et al. |
| 2009/0218593 A1 | 9/2009 | Kamikawa et al. |
| 2009/0250686 A1 | 10/2009 | Sato et al. |
| 2009/0301387 A1 | 12/2009 | D'Evelyn |
| 2009/0301388 A1 | 12/2009 | D'Evelyn |
| 2009/0309105 A1 | 12/2009 | Letts et al. |
| 2009/0309110 A1 | 12/2009 | Raring et al. |
| 2009/0320744 A1* | 12/2009 | D' Evelyn ............ C30B 7/00 117/81 |
| 2009/0320745 A1 | 12/2009 | D'Evelyn et al. |
| 2010/0001300 A1 | 1/2010 | Raring et al. |
| 2010/0003492 A1 | 1/2010 | D'Evelyn |
| 2010/0003942 A1 | 1/2010 | Ikeda et al. |
| 2010/0025656 A1 | 2/2010 | Raring et al. |
| 2010/0031872 A1 | 2/2010 | D'Evelyn |
| 2010/0031873 A1 | 2/2010 | D'Evelyn |
| 2010/0031874 A1 | 2/2010 | D'Evelyn |
| 2010/0031875 A1 | 2/2010 | D'Evelyn |
| 2010/0031876 A1 | 2/2010 | D'Evelyn |
| 2010/0032691 A1 | 2/2010 | Kim |
| 2010/0075175 A1 | 3/2010 | Poblenz et al. |
| 2010/0104495 A1 | 4/2010 | Kawabata et al. |
| 2010/0108985 A1 | 5/2010 | Chung et al. |
| 2010/0109030 A1 | 5/2010 | Krames et al. |
| 2010/0109126 A1 | 5/2010 | Arena |
| 2010/0117101 A1 | 5/2010 | Kim et al. |
| 2010/0117118 A1 | 5/2010 | Dabiran et al. |
| 2010/0147210 A1 | 6/2010 | D'Evelyn |
| 2010/0151194 A1 | 6/2010 | D'Evelyn |
| 2010/0189981 A1 | 7/2010 | Poblenz et al. |
| 2010/0295088 A1 | 11/2010 | D'Evelyn et al. |
| 2011/0017298 A1 | 1/2011 | Lee |
| 2011/0062415 A1 | 3/2011 | Ohta et al. |
| 2011/0064103 A1 | 3/2011 | Ohta et al. |
| 2011/0100291 A1 | 5/2011 | D'Evelyn |
| 2011/0108081 A1 | 5/2011 | Werthen et al. |
| 2011/0121331 A1 | 5/2011 | Simonian et al. |
| 2011/0175200 A1 | 7/2011 | Yoshida |
| 2011/0183498 A1 | 7/2011 | D'Evelyn |
| 2011/0220912 A1 | 9/2011 | D'Evelyn |
| 2011/0256693 A1 | 10/2011 | D'Evelyn et al. |
| 2011/0262773 A1 | 10/2011 | Poblenz et al. |
| 2012/0000415 A1 | 1/2012 | D'Evelyn et al. |
| 2012/0007102 A1 | 1/2012 | Feezell et al. |
| 2012/0025231 A1 | 2/2012 | Krames et al. |
| 2012/0073494 A1 | 3/2012 | D'Evelyn |
| 2012/0091465 A1 | 4/2012 | Krames et al. |
| 2012/0118223 A1 | 5/2012 | D'Evelyn |
| 2012/0119218 A1 | 5/2012 | Su |
| 2012/0137966 A1 | 6/2012 | D'Evelyn et al. |
| 2012/0187412 A1 | 7/2012 | D'Evelyn et al. |
| 2012/0199952 A1 | 8/2012 | D'Evelyn et al. |
| 2013/0119401 A1 | 5/2013 | D'Evelyn et al. |
| 2013/0251615 A1 | 9/2013 | D'Evelyn et al. |
| 2013/0323490 A1 | 12/2013 | D'Evelyn et al. |
| 2014/0065360 A1 | 3/2014 | D'Evelyn et al. |

FOREIGN PATENT DOCUMENTS

| | | |
|---|---|---|
| WO | WO 2004/030061 | 4/2004 |
| WO | WO 2006/038467 | 4/2006 |
| WO | 2006/057463 | 6/2006 |
| WO | 2007/004495 | 1/2007 |
| WO | WO 2010/068916 | 6/2010 |
| WO | 2012/016033 | 2/2012 |

OTHER PUBLICATIONS

Callahan et al., 'Synthesis and Growth of Gallium Nitride by the Chemical Vapor Reaction Process (CVRP)', MRS Internet Journal Nitride Semiconductor Research, vol. 4, No. 10, 1999, pp. 1-6.

Copel et al., 'Surfactants in Epitaxial Growth', Physical Review Letters, Aug. 7, 1989, vol. 63, No. 6, p. 632-635.

Dorsaz et al., 'Selective oxidation of AlInN Layers for current confinement III-nitride devices', Applied Physics Letters, vol. 87, 2005, pp. 072102.

Ehrentraut et al., 'The ammonothermal crystal growth of gallium nitride—A technique on the up rise', Proceedings IEEE, 2010, 98(7), pp. 1316-1323.

Fang., 'Deep centers in semi-insulating Fe-doped native GaN substrates grown by hydride vapour phase epitaxy', Physica Status Solidi, vol. 5, No. 6, 2008, pp. 1508-1511.

Fujito et al., 'Development of Bulk GaN Crystals and Nonpolar/Semipolar Substrates by HVPE', MRS Bulletin, May 2009, vol. 34, No. 5, pp. 313-317.

Gladkov et al., 'Effect of Fe doping on optical properties of freestanding semi-insulating HVPE GaN:Fe', Journal of Crystal Growth, 312, 2010, pp. 1205-1209.

Grzegory, 'High pressure growth of bulk GaN from Solutions in gallium', Journal of Physics Condensed Matter, vol. 13, 2001, pp. 6875-6892.

Lu et al., 'Structure of the Ci-passivated GaAs(111) surface', Physical Review B, Nov. 15, 1998, vol. 58, No. 20, pp. 13820-13823.

Massies et al., 'Surfactant mediated epitaxial growth of InxGa1-xAs on GaAs (001)', Applied Physics Letters, vol. 61, No. 1, Jul. 6, 1992, pp. 99-101.

Moutanabbir, 'Bulk GaN Ion Cleaving', Journal of Electronic Materials, vol. 39, 2010, pp. 482-488.

Oshima et al., 'Thermal and Optical Properties of Bulk GaN Crystals Fabricated Through Hydride Vapor Phase Epitaxy With Void-Assisted Separation', Journal of Applied Physics, vol. 98, No. 10, Nov. 18, 2005, pp. 103509-1-103509-4.

International Search Report & Written Opinion of PCT Application No. PCT/US2009/067745, dated Feb. 5, 2010, 9 pages total.

Porowski, 'Near Defect Free GaN Substrates', Journal of Nitride Semiconductor, 1999, pp. 1-11.

Sharma et al., Vertically oriented GaN-based air-gap distributed Bragg reflector structure fabricated using band-gap-selective photoelectrochemical etching, Applied Physics Letters, vol. 87, 2005, pp. 051107.

Sumiya et al., 'High-pressure synthesis of high-purity diamond crystal', Diamond and Related Materials, 1996, vol. 5, pp. 1359-1365.

Communication from the Polish Patent Office re P394857 dated Aug. 14, 2013, 2 pages.

Wang et al , 'Ammonothermal Growth of GaN Crystals in Alkaline Solutions', Journal of Crystal Growth, vol. 287, 2006, pp. 376-380.

USPTO Office Action for U.S. Appl. No. 12/133,365 dated May 13, 2013, 23 pages.

USPTO Office Action for U.S. Appl. No. 12/133,365 dated Aug. 21, 2013, 29 pages.

USPTO Office Action for U.S. Appl. No. 12/334,418 dated Sep. 17, 2013, 27 pages.

USPTO Office Action for U.S. Appl. No. 12/497,969 dated May 16, 2013, 22 pages.

(56) References Cited

OTHER PUBLICATIONS

USPTO Office Action for U.S. Appl. No. 12/497,969 dated Sep. 6, 2013, 21 pages.
USPTO Office Action for U.S. Appl. No. 12/636,683 dated Jun. 12, 2013, 15 pages.
USPTO Office Action for U.S. Appl. No. 12/636,683 dated Aug. 16, 2013, 16 pages.
USPTO Office Action for U.S. Appl. No. 12/697,171 dated Jun. 20, 2013, 17 pages.
USPTO Office Action for U.S. Appl. No. 12/697,171 dated Aug. 20, 2013, 17 pages.
USPTO Office Action for U.S. Appl. No. 12/891,668 dated Jan. 10, 2013, 31 pages.
USPTO Notice of Allowance for U.S. Appl. No. 12/891,668 dated Mar. 20, 2013, 14 pages.
USPTO Notice of Allowance for U.S. Appl. No. 13/175,739 dated Mar. 21, 2013, 6 pages.
USPTO Office Action for U.S. Appl. No. 13/272,981 dated Mar. 20, 2013, 19 pages.
USPTO Office Action for U.S. Appl. No. 13/272,981 dated Aug. 15, 2013, 13 pages.
USPTO Office Action for U.S. Appl. No. 13/346,507 dated Dec. 21, 2012, 9 pages.
USPTO Notice of Allowance for U.S. Appl. No. 13/346,507 dated Apr. 22, 2013, 8 pages.
USPTO Notice of Allowance for U.S. Appl. No. 13/548,931 dated Jun. 3, 2013, 11 pages.
USPTO Office Action for U.S. Appl. No. 13/472,356 dated Dec. 9, 2013 (11 pages).
USPTO Office Action for U.S. Appl. No. 12/133,365 dated Feb. 20, 2014, 32 pages.
USPTO Office Action for U.S. Appl. No. 12/636,683 dated Feb. 24, 2014, 16 pages.
USPTO Notice of Allowance for U.S. Appl. No. 13/272,981 dated Mar. 13, 2014, 10 pages.
Roder et al., 'Temperature dependence of the thermal expansion of GaN', Physics Review B, vol. 72., No. 085218, Aug. 24, 2005, 6 pages.
USPTO Office Action for U.S. Appl. No. 13/013,697 dated Jun. 9, 2014 (5 pages).
USPTO Office Action for U.S. Appl. No. 13/041,199 dated Apr. 29, 2014 (12 pages).
Communication from the Chinese Patent Office re 200980154756.9 dated Jun. 17, 2014 (10 pages).
USPTO Office Action for U.S. Appl. No. 12/484,095 dated Aug. 29, 2014 (10 pages).
USPTO Notice of Allowance for U.S. Appl. No. 13/013,697 dated Aug. 27, 2014 (5 pages).
USPTO Notice of Allowance for U.S. Appl. No. 13/041,199 dated Sep. 9, 2014 (9 pages).
USPTO Office Action for U.S. Appl. No. 13/160,307 dated Jun. 26, 2014 (19 pages).
USPTO Office Action for U.S. Appl. No. 13/894,220 dated Jul. 31, 2014 (9 pages).
USPTO Notice of Allowance for U.S. Appl. No. 12/534,843 dated Jan. 24, 2013.
Communication from the Polish Patent Office re P394857 dated Jan. 22, 2013, 2 pages.
USPTO Notice of Allowance for U.S. Appl. No. 12/634,665 dated Feb. 15, 2013.
USPTO Office Action for U.S. Appl. No. 13/041,199 dated Mar. 12, 2013.
USPTO Notice of Allowance for U.S. Appl. No. 13/226,249 dated Feb. 21, 2013.
Choi et al., '2.51 microcavity InGaN light-emitting diodes fabricated by a selective dry-etch thinning process', Applied Physics Letters, 2007, 91(6), 061120.
D'Evelyn et al., 'Bulk GaN Crystal Growth by the High-Pressure Ammonothermal Method,' Journal of Crystal Growth, vol. 300, 2007, pp. 11-16.

Fukuda et al., 'Prospects for the Ammonothermal Growth of Large GaN Crystal,' Journal of Crystal Growth, vol. 305, 2007, pp. 304-310.
Iso et al., 'High Brightness Blue InGaN/GaN Light Emitting Diode on Nonpolar m-Plane Bulk GaN Substrate,' Japanese Journal of Applied Physics, 2007, vol. 46, No. 40, pp. L960-L962.
Lide et al., 'Thermal Conductivity of Ceramics and Other Insulating Materials,' CRC Handbook of Chemistry and Physics, 91st Edition, 2010-2011, pp. 12-203 and 12-204.
http://www.matbase.com/material/non-ferrous-metals/other/molybdenum/properties, Data Table for: Non-Ferrous Metals: Other Metals: Molybdenum, Mar. 28, 2011, pp. 1.
Pattison et al 'Gallium Nitride Based Microcavity Light Emitting Diodes With 2λ Effective Cavity Thickness', Applied Physics Letters, vol. 90, Issue 3, 031111 (2007) 3pg.
Sarva et al., 'Dynamic Compressive Strength of Silicon Carbide Under Uniaxial Compression,' Material Sciences and Engineering, vol. A317, 2001, pp. 140-144.
Tyagi et al., 'Semipolar (1011) InGaN/GaN Laser Diodes on Bulk GaN Substrates,' Japanese Journal of Applied Physics, vol. 46, No. 19, 2007, pp. L444-L445.
Weisbuch et al., 'Recent results and latest views on microcavity LEDs', Light-Emitting Diodes: Research, Manufacturing, and Applications VIII, ed. By S.A. Stockman et al., Proc. SPIE, vol. 5366, p. 1-19 (2004).
USPTO Office Action for U.S. Appl. No. 12/133,364 dated Nov. 26, 2010.
USPTO Office Action for U.S. Appl. No. 12/133,364 dated Jun. 1, 2011.
USPTO Notice of Allowance for U.S. Appl. No. 12/133,364 dated Oct. 11, 2011.
USPTO Office Action for U.S. Appl. No. 12/133,365 dated Jun. 9, 2011.
USPTO Office Action for U.S. Appl. No. 12/133,365 dated Oct. 18, 2011.
USPTO Office Action for U.S. Appl. No. 12/334,418 dated Apr. 5, 2011.
USPTO Office Action for U.S. Appl. No. 12/334,418 dated Oct. 19, 2011.
USPTO Office Action for U.S. Appl. No. 12/478,736 dated Sep. 27, 2011.
USPTO Office Action for U.S. Appl. No. 12/478,736 dated Feb. 7, 2012.
USPTO Notice of Allowance for U.S. Appl. No. 12/478,736 dated Apr. 23, 2012.
USPTO Notice of Allowance for U.S. Appl. No. 12/478,736 dated Oct. 9, 2012.
USPTO Office Action for U.S. Appl. No. 12/484,095 dated Nov. 10, 2010.
USPTO Office Action for U.S. Appl. No. 12/484,095 dated Jul. 8, 2011.
USPTO Office Action for U.S. Appl. No. 12/497,969 dated Feb. 2, 2012.
USPTO Office Action for U.S. Appl. No. 12/497,969 dated Jul. 5, 2012.
USPTO Office Action for U.S. Appl. No. 12/534,838 dated May 3, 2011.
USPTO Office Action for U.S. Appl. No. 12/534,838 dated Jan. 13, 2012.
USPTO Office Action for U.S. Appl. No. 12/534,838 dated Mar. 20, 2012.
USPTO Notice of Allowance for U.S. Appl. No. 12/534,838 dated Jun. 8, 2012.
USPTO Office Action for U.S. Appl. No. 12/534,843 dated Sep. 10, 2012.
USPTO Office Action for U.S. Appl. No. 12/534,844 dated Sep. 16, 2010.
USPTO Office Action for U.S. Appl. No. 12/534,844 dated Feb. 4, 2011.
USPTO Notice of Allowance for U.S. Appl. No. 12/534,849 dated Jul. 31, 2012.
USPTO Office Action for U.S. Appl. No. 12/534,857 dated Sep. 1, 2010.

(56) References Cited

OTHER PUBLICATIONS

USPTO Notice of Allowance for U.S. Appl. No. 12/534,857 dated May 27, 2011.
USPTO Office Action for U.S. Appl. No. 12/546,458 dated Jul. 20, 2011.
USPTO Notice of Allowance for U.S. Appl. No. 12/546,458 dated Nov. 28, 2011.
USPTO Office Action for U.S. Appl. No. 12/556,558 dated Sep. 16, 2010.
USPTO Notice of Allowance for U.S. Appl. No. 12/556,558 dated Mar. 22, 2011.
USPTO Office Action for U.S. Appl. No. 12/556,562 dated Sep. 15, 2010.
USPTO Office Action for U.S. Appl. No. 12/556,562 dated Mar. 21, 2011.
USPTO Notice of Allowance for U.S. Appl. No. 12/556,562 dated Jul. 27, 2011.
USPTO Office Action for U.S. Appl. No. 12/569,337 dated May 9, 2012.
USPTO Notice of Allowance for U.S. Appl. No. 12/569,337 dated Nov. 15, 2012.
USPTO Office Action for U.S. Appl. No. 12/569,841 dated Dec. 23, 2011.
USPTO Office Action for U.S. Appl. No. 12/569,844 dated Oct. 12, 2012.
USPTO Office Action for U.S. Appl. No. 12/634,665 dated Apr. 25, 2012.
USPTO Office Action for U.S. Appl. No. 12/634,665 dated Oct. 1, 2012.
USPTO Office Action for U.S. Appl. No. 12/724,983 dated Mar. 5, 2012.
USPTO Notice of Allowance for U.S. Appl. No. 12/754,886 dated May 17, 2012.
USPTO Notice of Allowance for U.S. Appl. No. 12/754,886 dated Jun. 5, 2012.
USPTO Notice of Allowance for U.S. Appl. No. 12/754,886 dated Jun. 20, 2012.
USPTO Office Action for U.S. Appl. No. 12/785,404 dated Mar. 6, 2012.
USPTO Notice of Allowance for U.S. Appl. No. 12/785,404 dated Jul. 16, 2012.
USPTO Office Action for U.S. Appl. No. 12/891,668 dated Sep. 25, 2012.
USPTO Office Action for U.S. Appl. No. 13/025,833 dated Jul. 12, 2012.
USPTO Office Action for U.S. Appl. No. 13/041,199 dated Nov. 30, 2012.
USPTO Office Action for U.S. Appl. No. 13/175,739 dated Dec. 7, 2012.
USPTO Office Action for U.S. Appl. No. 13/179,346 dated Aug. 17, 2012.
USPTO Office Action for U.S. Appl. No. 13/179,346 dated Dec. 13, 2012.
USPTO Office Action for U.S. Appl. No. 13/226,249 dated Oct. 10, 2012.
USPTO Notice of Allowance for U.S. Appl. No. 13/425,304 dated Aug. 22, 2012.

* cited by examiner

APPARATUS FOR LARGE VOLUME AMMONOTHERMAL MANUFACTURE OF GALLIUM NITRIDE CRYSTALS AND METHODS OF USE

The present application claims the benefit of priority to U.S. Patent Application No. 61/549,893 filed on Oct. 21, 2011.

FIELD

The present disclosure relates generally to techniques for an apparatus for processing supercritical fluids. More specifically, embodiments of the disclosure include techniques for configuring a material processing capsule disposed within a high-pressure apparatus enclosure.

BACKGROUND OF THE DISCLOSURE

Legacy crystal growth techniques (e.g., methods and supporting apparatus) that serve for processing supercritical fluids have unwanted limitations.

To eliminate or mitigate these limitations, techniques for improving a high pressure apparatus for crystal growth is highly desirable. Needed are improved techniques for configuring a material processing capsule disposed within a high-pressure apparatus enclosure.

BRIEF SUMMARY OF THE DISCLOSURE

According to the present disclosure, techniques related generally to an apparatus for processing supercritical fluids are provided. More specifically, embodiments of the disclosure include techniques for configuring a material processing capsule disposed within a high-pressure apparatus enclosure.

In a specific embodiment, the present disclosure provides a scalable apparatus to contain the reaction volume used in the synthesis of gallium nitride crystals using the ammonothermal method at temperatures up to 1200 degrees Celsius, and pressures up to 2000 MPa comprising of the features and improvements mentioned above and herein.

In a specific embodiment, the present disclosure provides an apparatus for processing material at an elevated pressure. The apparatus includes an upper crown member, a lower crown member, an upper restraint member, and a lower restraint member. The apparatus also has one or more radial restraint structures disposed between the upper restraint member and the lower restraint member. The apparatus includes at least a first tie rod coupled between the upper crown member and the lower restraint member and a second tie rod coupled between the lower crown member and the upper restraint member. Preferably, the first tie rod member and the second tie rod member are provided for an axial restraint of the stack of radial restraint structures. In optional embodiments, the one or more radial restraint structures comprise at least one continuous annular ceramic member or the one or more radial restraint structures comprise at least one radial segment or the one or more radial restraint structures comprises one or more high strength enclosures or the one or more radial restraint structures comprises a stack of two or more ring assemblies, the ring assemblies comprising a high strength enclosure ring and a ceramic ring or ceramic radial segment assembly.

In various embodiment, the apparatus can include variations. That is, the first tie rod is one of two or more first tie rods coupled between the upper crown member and the lower restraint member. The second tie rod is one of two or more second tie rods coupled between the lower crown member and the upper restraint member. The apparatus may also have a third rod coupled between the upper crown member and the second crown member.

In other embodiments, the apparatus has additional features to carry out the high pressure processing. The apparatus has a processing chamber disposed within a region of the one or more radial restraint structures. The apparatus also has a means or device for external cooling configured along a spatial region of the one or more radial restraint structures. Additionally, a heating member or heater is positioned between the processing chamber and the one or more radial restraint structures. Of course, there can be other variations.

In an alternative embodiment, the present disclosure provides an apparatus for growth of a gallium- and nitrogen-containing material. The apparatus includes a first crown plate structure comprising an opening region, which includes a first pattern configured to insert a capsule device there through, and a second crown plate structure operably coupled to the first crown plate structure to maintain a processing region between the first crown plate structure and the second crown plate structure. Preferably, the processing region is capable of housing the capsule device. The apparatus also has a crown insert structure configured to plug the opening region. The crown insert structure comprises a second pattern that is complementary with the first pattern. The second pattern is configured to be insertable into the first pattern for plugging the opening region when the crown insert structure is moved in a direction normal to the first crown structure; and is configured to be offset from the first pattern when rotated in a predetermined manner while the crown insert is engaged with the first pattern in the opening region such that the crown insert is substantially held in place with the first crown plate structure to plug the opening region and support an axial load.

In yet an alternative embodiment, the present disclosure provides an apparatus for growth of a gallium- and nitrogen-containing material. The apparatus has a first crown plate structure comprising an opening region, which includes a first pattern configured to insert a capsule device there through. Preferably, the first pattern comprises a first open region in communication with a second open region, which is larger than the first open region. The apparatus also has a second crown plate structure operably coupled to the first crown structure to maintain a processing region between the first crown plate structure and the second crown plate structure. The processing region is capable of housing the capsule device. The apparatus has a crown insert device configured to plug the opening region. The crown insert device comprises a plug member, a plurality of locking members, and at least one key member. Preferably, the plurality of locking members are configured with the key member to hold the plug member within a vicinity of the opening region to plug the opening region with the crown insert device and support an axial load.

The present disclosure achieves these benefits and others in the context of known process technology. However, a further understanding of the nature and advantages of the present disclosure may be realized by reference to the latter portions of the specification and attached drawings.

DETAILED DESCRIPTION OF THE DISCLOSURE

To improve on legacy techniques, several types of apparatus with capability for pressures and temperatures well in excess of that of conventional autoclaves are disclosed. The apparatus supports improved scalability and other improvements relative to a zero-stroke press. In one apparatus, a series of wedge-shaped radial ceramic segments are placed between a heater, which surrounds a capsule, and a high-strength enclosure. The wedge segments enable a reduction in the pressure and temperature to which the inner diameter of the high-strength enclosure is exposed, as compared to the corresponding values for the capsule. Fabrication and use of these ceramic wedge-shaped radial segments, however, can be difficult and expensive, and the maximum volume may be limited. Additionally, conventional techniques to enclose the capsule and maintain the processing region have been limited. These and other limitations of conventional apparatus may be described throughout the present specification. According to the present disclosure, techniques related generally to an apparatus for growing crystals or processing materials in supercritical fluids are provided. More specifically, embodiments of the disclosure include techniques for configuring a material processing capsule disposed within a high-pressure apparatus enclosure.

According to the present disclosure, techniques related generally to an apparatus for growing crystals or processing materials in supercritical fluids are provided. More specifically, embodiments of the disclosure include techniques for configuring a material processing capsule disposed within a high-pressure apparatus enclosure.

Figure 1:
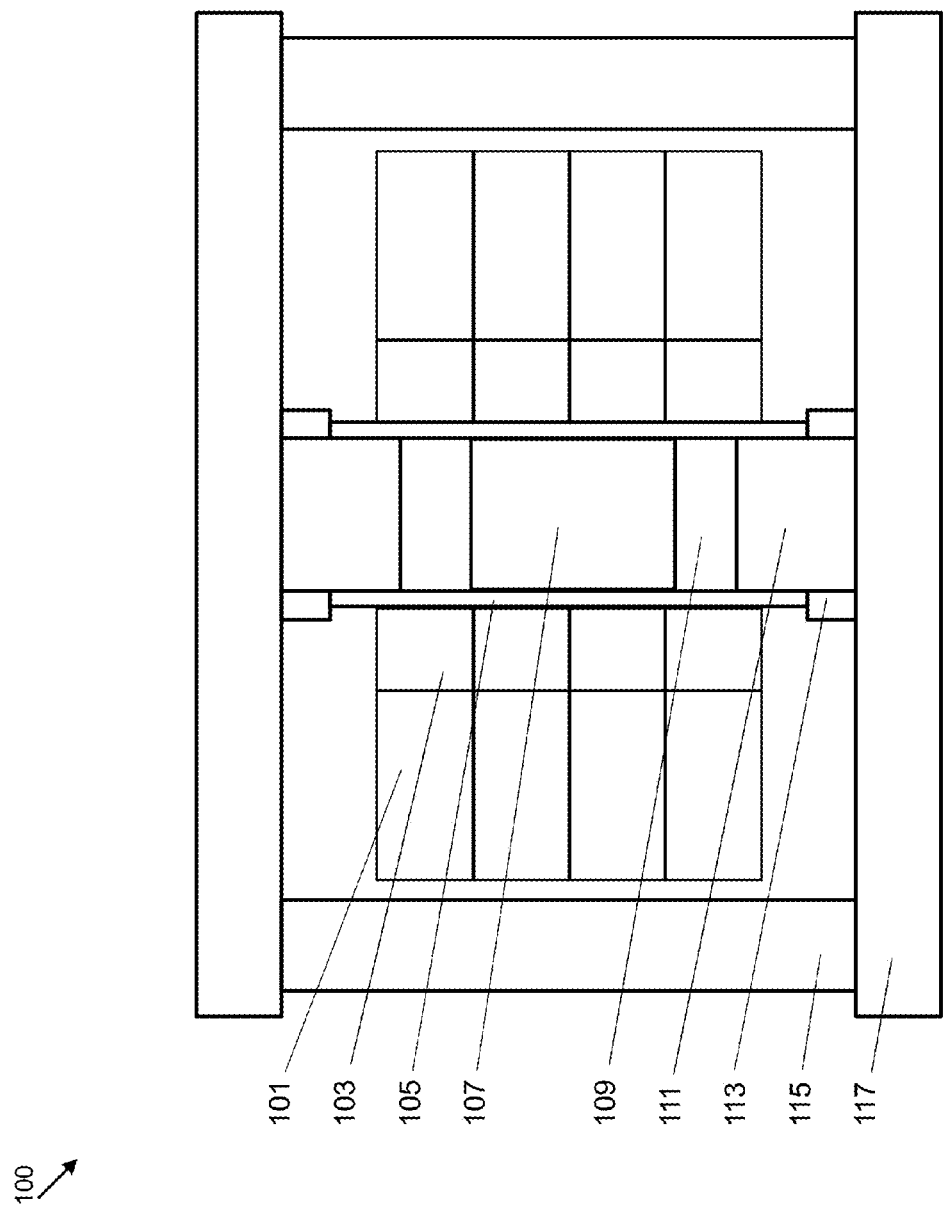
FIG. 1 is a simplified diagram illustrating a high pressure apparatus, according to an embodiment of the present disclosure.

In a specific embodiment, the present disclosure provides an apparatus and methods to contain the reaction vessel in which gallium nitride crystals (henceforth referred to as bulk crystals) can be grown using the ammonothermal method at high pressure and temperature. The apparatus provides adequate containment in all directions which, for a typical cylindrical vessel, can be classified as radial and axial. Furthermore, depending on the specifics of the design parameters, the apparatus is capable of operating at a temperature up to 1200 degrees Celsius, a pressure up to 2000 MPa, and for whatever length of time is necessary to grow satisfactory bulk crystals, for example, between about 1 hour and about 180 days. Referring to FIG. 1, the radial constraint in the present apparatus may be provided by several stacked ring assemblies, each of which may in turn be assembled from some combination of embodiments of a high strength enclosure ring 101, embodiments of a ceramic ring 103, and embodiments of ceramic radial wedge segments. These stacked ring assemblies will henceforth be collectively referred to as the die stack. The design of the apparatus is scalable to contain reaction volumes larger than 100 cubic centimeters (cc) and has been successfully scaled up to contain a reaction volume larger than 13 liters. One skilled in the art may employ the concepts, principles, and analyses disclosed in this disclosure to design apparatus for the containment of even larger volumes, for example, larger than about 25 liters, larger than about 50 liters, larger than about 100 liters, larger than about 1000 liters, or larger than about 10,000 liters, and/or higher temperature and pressures. Further details of the apparatus can be found throughout the present specification and more particularly below.

FIG. 1 is a simplified diagram illustrating a high pressure apparatus 100 according to an embodiment of the present disclosure. This diagram is merely an illustration and should not unduly limit the scope of the claims herein.

The apparatus comprises a stack of two or more ring assemblies 100, comprising a high strength enclosure ring 101 and a ceramic ring 103. The stack may include greater than 2, greater than 5, greater than 10, greater than 20, greater than 30, greater than 50, or greater than 100 ring assemblies. In certain embodiments, a stack includes from 2-10 ring assemblies, from 10 to 20, from 20 to 30, from 30 to 40, from 40 to 50, and in certain embodiments, from 50 to 100 ring assemblies. The stack surrounds heater or heating member 105 and capsule 107 and may be supported mechanically by at least one support plate (not shown, but see discussion below). In other words, the heating member or heater may be positioned between the capsule and one or more radial restraint structures comprise a high strength enclosure ring and a ceramic ring. The stack may provide radial confinement for pressure generated within capsule 107 and transmitted outward through heater 105. The interior of heater 105 may define a processing chamber, into which capsule 107 may be placed. In the case that the ring assemblies in the die stack are comprised of high strength enclosure ring 101 and ceramic ring 103, there may be an interference fit between the two members in each ring assembly. Means for external cooling of the one or more ring assemblies or radial restraints may be provided.

Axial confinement of pressure generated within capsule 107 may be provided by end plugs 111, crown members 117, and tie rods or tie rod fasteners 115. End plugs 111 may comprise, for example, zirconium oxide or zirconia. Alternative end plug materials include, for example, magnesium oxide, aluminum oxide, silicon oxide, silicon carbide, tungsten carbide, steel, nickel alloys, salts, and phyllosilicate minerals such as aluminum silicate hydroxide or pyrophyllite, according to a specific embodiment. End plugs 111 may be surrounded by end plug jackets 113. End plug jackets 113 may provide mechanical support and/or radial confinement for end plugs 111. End plug jackets 113 may also provide mechanical support and/or axial confinement for heater 105. End plug jackets 113 may comprise, for example, steel, stainless steel, an iron-based alloy, a nickel-based alloy, or the like.

Crown members 117 and tie rod fasteners 115 may comprise a material, for example, selected from a group consisting of steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, zirconium and its alloys, titanium and its alloys, and other materials commonly known as Monel®, Inconel®, Hastelloy®, Udimet® 500, Stellite®, Rene® 41, and Rene® 88.

Apparatus 100 may include a pressure transmission medium 109 proximate to the axial ends of capsule 107 and to end plugs 111 according to a specific embodiment. The pressure transmission medium may comprise, for example, sodium chloride, other salts, or phyllosilicate minerals such as aluminum silicate hydroxide or pyrophyllite, or other materials, according to a specific embodiment. In certain embodiments, pressure transmission medium 109 may comprise one or more of metal halides, such as NaCl, NaBr, AgCl, AgBr, $CaF_2$, $SrF_2$, graphite, hexagonal boron nitride, talc, soapstone, gypsum, limestone, alabaster, molybdenum disulfide, calcium carbonate, magnesium oxide, zirconium oxide, merylinite clay, bentonite clays, sodium silicate, or a combination of any of the foregoing.

The illustrated apparatus 100 can be used to grow crystals under pressure and temperature conditions desirable for crystal growth, e.g., gallium nitride crystals under related process conditions. The high-pressure apparatus 100 can include one or more structures operable to support the heating member 105 radially, axially, or both radially and axially. The support structure in one embodiment thermally insulates the apparatus 100 from the ambient environment, and such insulation may enhance or improve process stability, and maintain and control a desired temperature profile.

Figure 2:
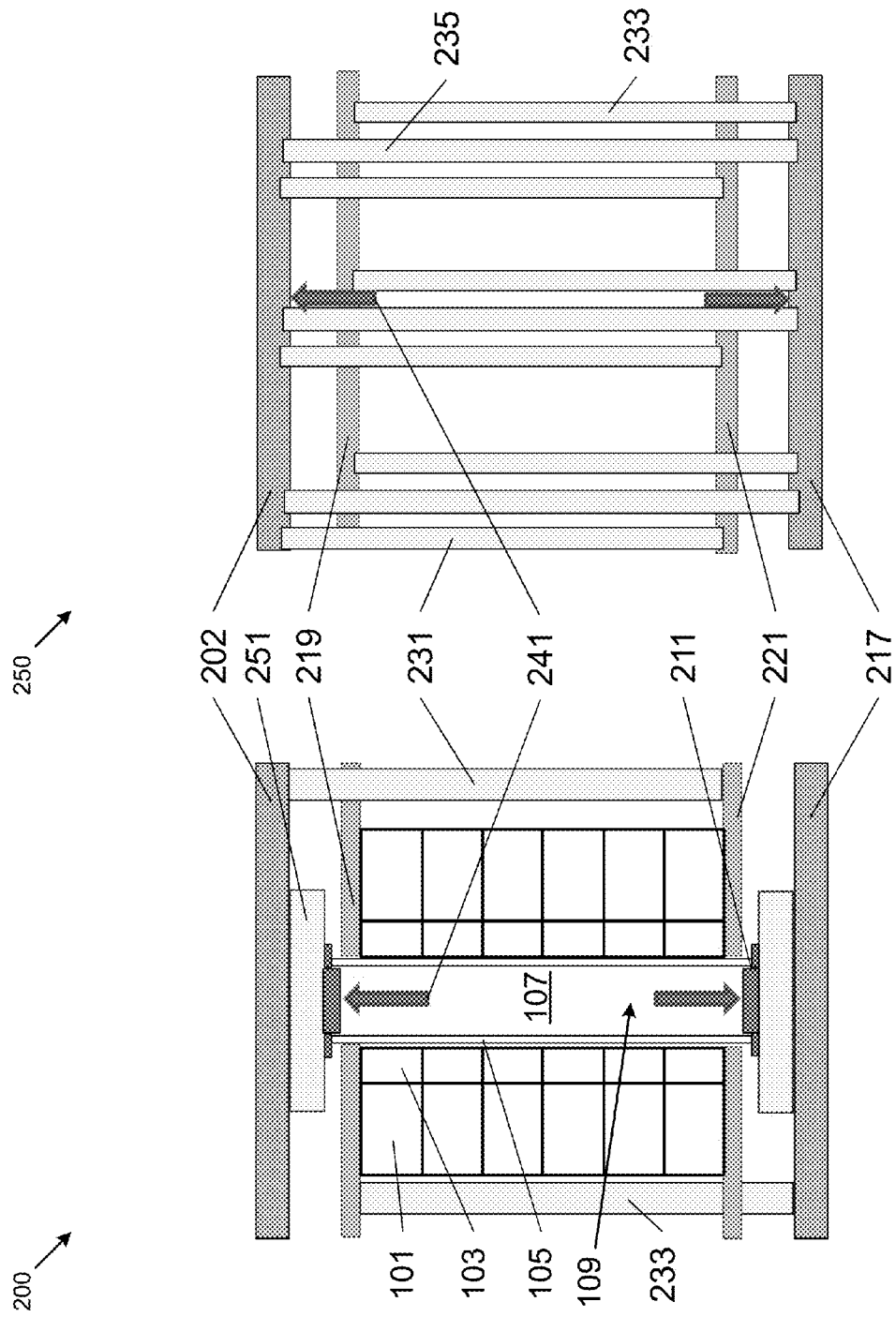
FIG. 2A is a simplified diagram illustrating a high pressure apparatus having tie rod structures, according to embodiments of the present disclosure.
FIG. 2B is a simplified diagram illustrating a high pressure apparatus having tie rod structures, according to embodiments of the present disclosure.

FIG. 2A 200 and FIG. 2B 250 are simplified diagrams illustrating a high pressure apparatus having tie rod structures according to embodiments of the present disclosure. These diagrams are merely illustrations and should not unduly limit the scope of the claims herein. FIG. 2A and FIG. 2B show apparatus 200 and 250, respectively, for processing material at elevated pressure. The apparatus includes an upper crown member 202, a lower crown member 217, an upper die restraint member 219, and a lower die restraint member 221.

In a specific embodiment, the apparatus, to provide radial restraint, also has one or more ring assemblies, each of which may in turn be assembled from a combination of any number of embodiments of high strength enclosure ring 101, ceramic ring 103, and ceramic radial wedge segments, disposed between the upper die restraint member and the lower die restraint member. The apparatus may further comprise a heater or heating member 105, upper and lower end plugs 111, and upper and lower crown inserts 251.

The apparatus includes at least a first tie rod 231 or set of first tie rods coupled between the upper crown plate or upper crown member 202 and the lower die restraint member 221, and a second tie rod 233 or set of second tie rods coupled between the lower crown member 217 and the upper die restraint member 219. In one specific embodiment, shown schematically in FIG. 2A, the entire axial load 241 is generated within the heater 205, for example, by the process pressure associated with a supercritical fluid contained within a capsule (not shown), compresses the die stack. In another specific embodiment, as shown in FIG. 2B, the apparatus also includes at least a third tie rod 235 or set of third tie rods coupled between the upper crown member and the lower crown member. In this embodiment the axial load 241 is split between compression of the stack of radial restraint structures and tensile loading of the third set of tie rods. The fraction of the axial load that compresses the stack of radial restraint structures may be adjusted by means of the number and diameters of each set of tie rods, the dimensions of the radial restraint structures, the pre-operation tensile loading of each tie rod, and the elastic moduli of each material in the structure, among other factors. In still another embodiment, the stack of radial restraint members is axially loaded by pre-loading one or more tie rods or axial restraint members coupled between an upper crown member (or upper die restraint member) and a lower crown member (or lower die restraint member).

In certain embodiments, each set of first tie rods 231, second tie rods 233, and third tie rods 235 is symmetrically placed about the axis of the apparatus, so that axial mechanical loads are shared approximately equally between the tie rods comprising each set.

In certain embodiments, the first tie rod member and the second tie rod member are provided for an axial restraint of the die stack. In optional embodiments, the one or more radial restraint structures comprise at least one ceramic ring 103. The one or more radial restraint structures may comprise at least one radial segment. The one or more radial restraint structures may comprise one or more high strength enclosure rings. The one or more radial restraint structures may comprise a stack of two or more ring assemblies, the ring assemblies comprising a high strength enclosure ring 101 and a ceramic ring 103.

In certain embodiments, closeable openings are provided in the crown members to allow for insertion and removal of capsules, heaters, and other components while retaining capability for supporting large axial loads.

Figure 3:
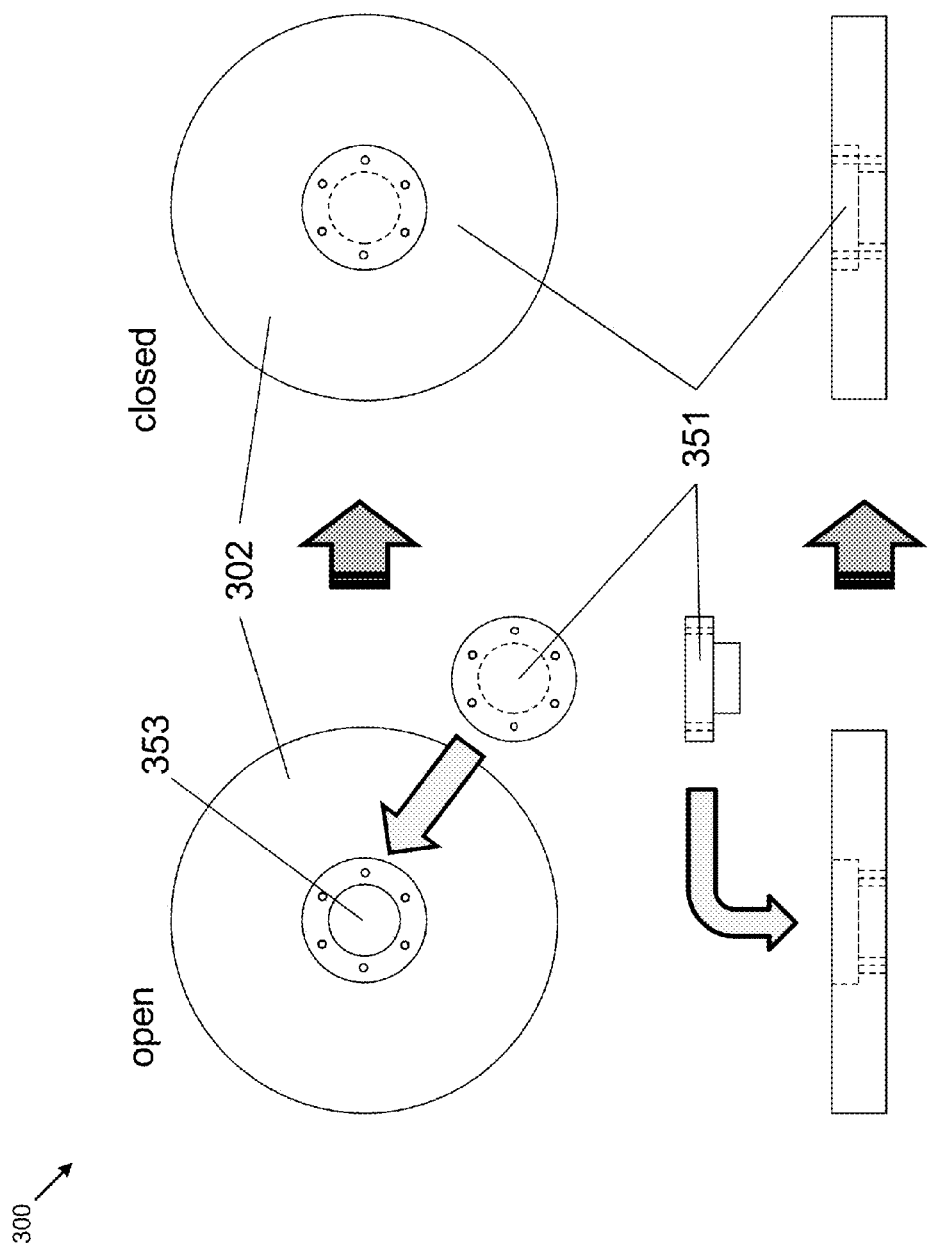
FIG. 3 is a simplified perspective diagram of a crown insert apparatus configured as a flange structure, according to an embodiment of the present disclosure.

FIG. 3 is a simplified perspective diagram 300 of a crown insert apparatus configured as a flange structure. In one set of embodiments, shown schematically in FIG. 3, openings 353 in the crown members 302 may be closed by means of flanges 351 that are coupled by means of bolts or other fasteners. However, in this embodiment the entire axial load may be supported by the fasteners, in tension, which may provide a limit to the maximum allowable axial load that is lower than desired.

Figure 4:
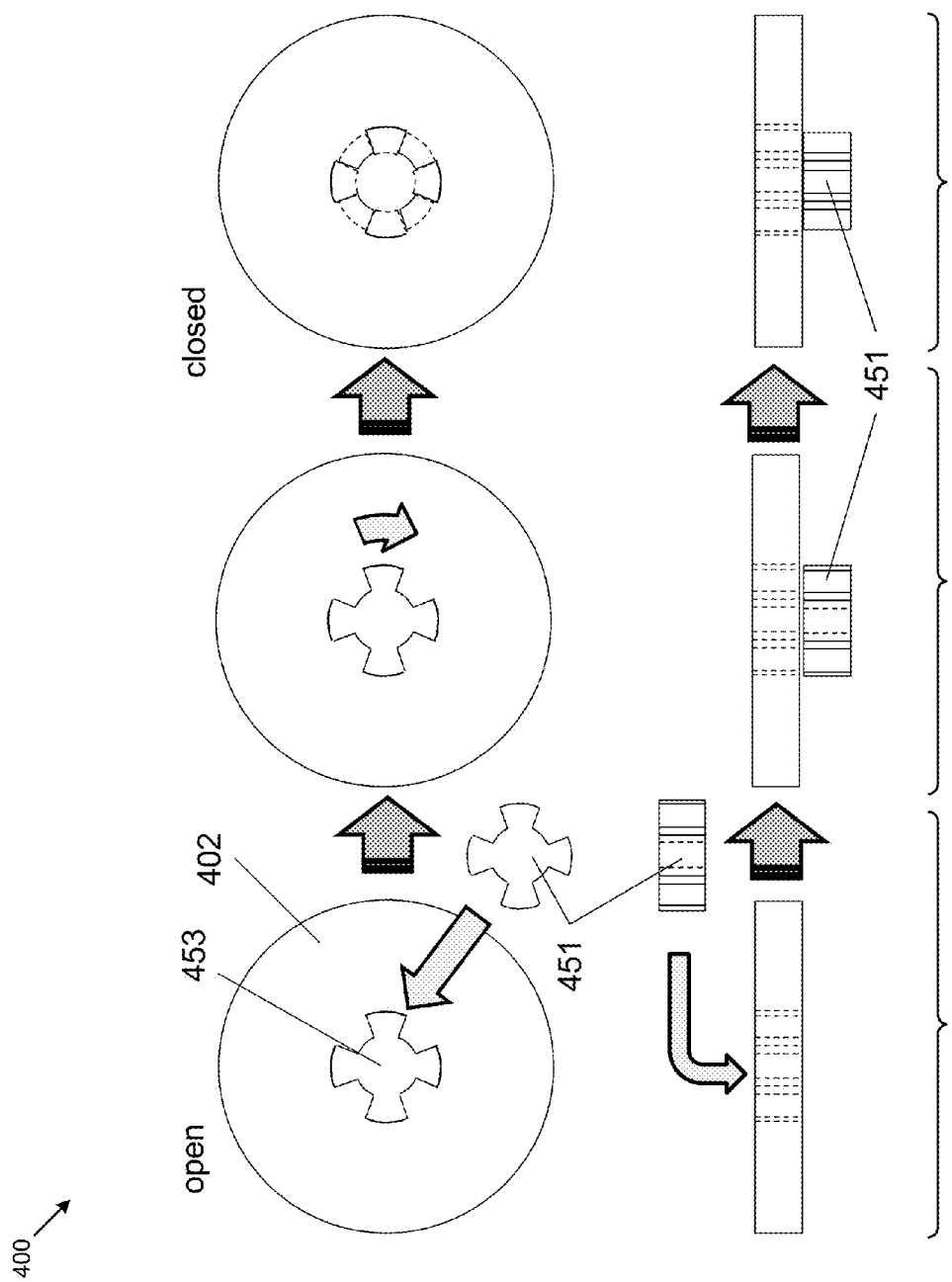
FIGS. 4A, 4B, and 4C are simplified diagrams of a crown insert apparatus configured as a fan structure, according to an embodiment of the present disclosure.

FIGS. 4A, 4B, and 4C are simplified diagrams, showing separate end and edge views, of a crown insert apparatus 400 configured as a fan structure. These diagrams are merely an illustration and should not unduly limit the scope of the claims herein. In a specific embodiment, the present disclosure provides an apparatus for growth of a gallium and nitrogen containing material.

The apparatus includes a first crown member 402 (also referred to as crown plate structure) comprising an opening region 453, which includes a first pattern configured to insert a capsule device there through. The apparatus has a second crown member or plate structure operably coupled to the first crown plate structure to maintain a processing region between the first crown plate structure and the second crown plate structure, for example, by means of one or more sets of tie rods. Preferably, the processing region is capable of housing the capsule device. The capsule device is designed to process gallium and nitrogen containing crystals.

In a specific embodiment, the apparatus also has a crown insert structure 451 configured to plug the opening region 453. The crown insert structure 451 comprises a second pattern that is complementary with the first pattern of opening region 453. The second pattern is configured to be insertable into the first pattern for plugging the opening region 453 when the crown insert structure 451 is moved in a direction normal to the first crown structure; and is configured to be off-set from the first pattern when rotated in a predetermined manner while the crown insert is engaged with the first pattern in the opening region such that the crown insert is substantially held in place with the first crown plate structure to plug the opening region and support an axial load.

As shown, the first pattern comprises a first pair of opposing extension regions and the second pattern comprises a second pair of opposing extension regions. Additionally, the first pattern comprises a plurality of first extension regions and the second pattern comprises a plurality of second extension regions. Of course, there can be other variations, modifications, and alternatives.

In one specific embodiment, illustrated schematically in FIG. 4A, crown insert structure 451 is inserted through opening region 453 in crown member 402, forming the configuration illustrated schematically in FIG. 4B. The crown insert structure 451 is then rotated, by approximately 45 degrees in the case illustrated, to provide a closed configuration as shown schematically in FIG. 4C. In the open configuration a capsule, a heater, and other components may be inserted into or removed from the high pressure apparatus. In the closed configuration the combination of the crown members, the crown inserts, and the tie rods are capable of supporting a large axial load.

In a specific embodiment, the crown plate structures and/or the crown insert structures are manufactured of a suitable material to withstand mechanical, chemical, and thermal forces. In certain embodiments, the first crown plate structure and the second crown plate structure are made of a material selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, or cobalt and its alloys or superalloys. In a specific embodiment, the crown insert structure comprises a material selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, and cobalt and its alloys or superalloys.

In a specific embodiment, the apparatus also includes fastening devices. The fastening devices are provided to hold the crown insert structure in place with the first crown structure. Again, there can be other variations, modifications, and alternatives. In a specific embodiment, the apparatus is also configured with specific spatial orientations. That is, an angle between the normal to the planes of contact between the first pattern and the second pattern and the normal to the first crown plate structure lies between about 5 degrees and about 60 degrees, but can be slightly greater or less. In a specific embodiment, an apparatus can withstand a suitable load, such as those greater than about 500 tons, greater than about 1000 tons, greater than about 10,000 tons, or greater than about 100,000 tons. In certain embodiments, an apparatus can withstand a load from about 100 to 500 tons, from 500 tons to 1,000 tons, from 1,000 tons to 10, 10,000 tons, from 10,000 tons to 100,000 tons, from 100,000 tons to 250,000 tons, and in certain embodiments, from 250,000 tons to 500,000 tons. Further details of other embodiments of the present disclosure can be found throughout the present specification and more particularly below.

Figure 5:
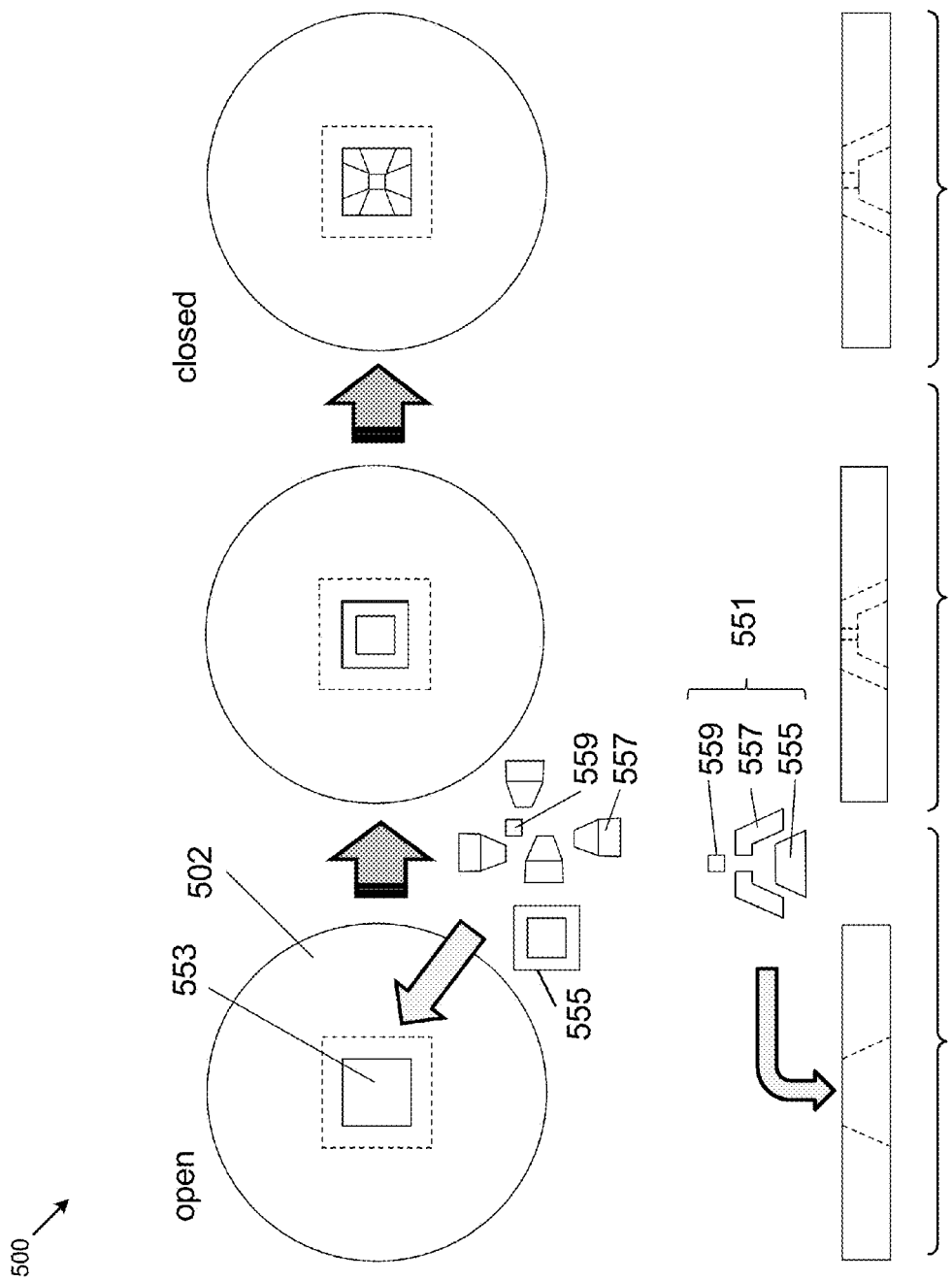
FIGS. 5A, 5B, and 5C are simplified diagrams of a crown insert apparatus configured as a wedge structure, according to an embodiment of the present disclosure.

FIGS. 5A, 5B, and 5C are simplified diagrams of a crown insert apparatus 500 configured as a wedge structure. These diagrams are merely an illustration and should not unduly limit the scope of the claims herein.

As shown in FIGS. 5A, 5B, and 5C, the apparatus is for growth of a gallium and nitrogen containing material. The apparatus has a first crown plate structure 502 comprising an opening region 553, which includes a first pattern configured to insert a capsule device there through. In certain embodiments, the first pattern comprises a first open region in communication with a second open region, which is larger than the first open region. The apparatus also has a second crown plate structure operably coupled to the first crown structure to maintain a processing region between the first crown plate structure and the second crown plate structure.

Depending upon the embodiment, the crown plate is made of suitable materials capable of mechanical, chemical, and thermal stress. For example, the first crown plate structure may be made of a material selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, or cobalt and its alloys or superalloys. The second crown structure may be made of a material selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, and cobalt and its alloys or superalloys. The components comprising the crown insert device may be made of a material selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, and cobalt and its alloys or superalloys.

In a specific embodiment, the processing region is capable of housing a capsule device. The apparatus has a crown insert device 551 configured to plug the opening region 553. The crown insert device 551 comprises a plug member 555, a plurality of locking members 557, and at least one key member 559. As shown, the plug member 555 is configured as a truncated pyramid shape.

In certain embodiments, the plurality of locking members 557 are configured with the key member 559 to hold the plug member 555 within a vicinity of the opening region 553 to plug the opening region 553 with the crown insert device 551 and support an axial load. Additionally, each of the locking members 557 may be configured as a sleeve to be disposed between a portion of the plug member 555 and the first pattern. The key member 559 can also include variations, such as a square or rectangular shape.

Referring again to FIG. 5A, to close opening region 553 in crown plate structure 502, plug member 555 is inserted through opening region 553, as shown schematically in FIG. 5B. Locking members 557 are then slidingly inserted into the gaps between plug member 555 and opening region 553, and then held in place by key member 559, as shown schematically in FIG. 5C. The sequence may be reversed to open the opening region 553. In the open configuration a capsule, a heater, and other components may be inserted into or removed from the high pressure apparatus. In the closed configuration the combination of the crown members, the crown insert assemblies, and the tie rods are capable of supporting a large axial load.

In a specific embodiment, the apparatus is also configured with specific spatial orientations. That is, an angle between the normal to the planes of contact between the first pattern and the second pattern and the normal to the first crown plate structure lies between about 5 degrees and about 60 degrees, but can be slightly greater or less. In a specific embodiment, the apparatus can withstand a suitable load, such as those greater than about 500 tons. Further details of other embodiments of the present disclosure can be found throughout the present specification and more particularly below.

Figure 6:
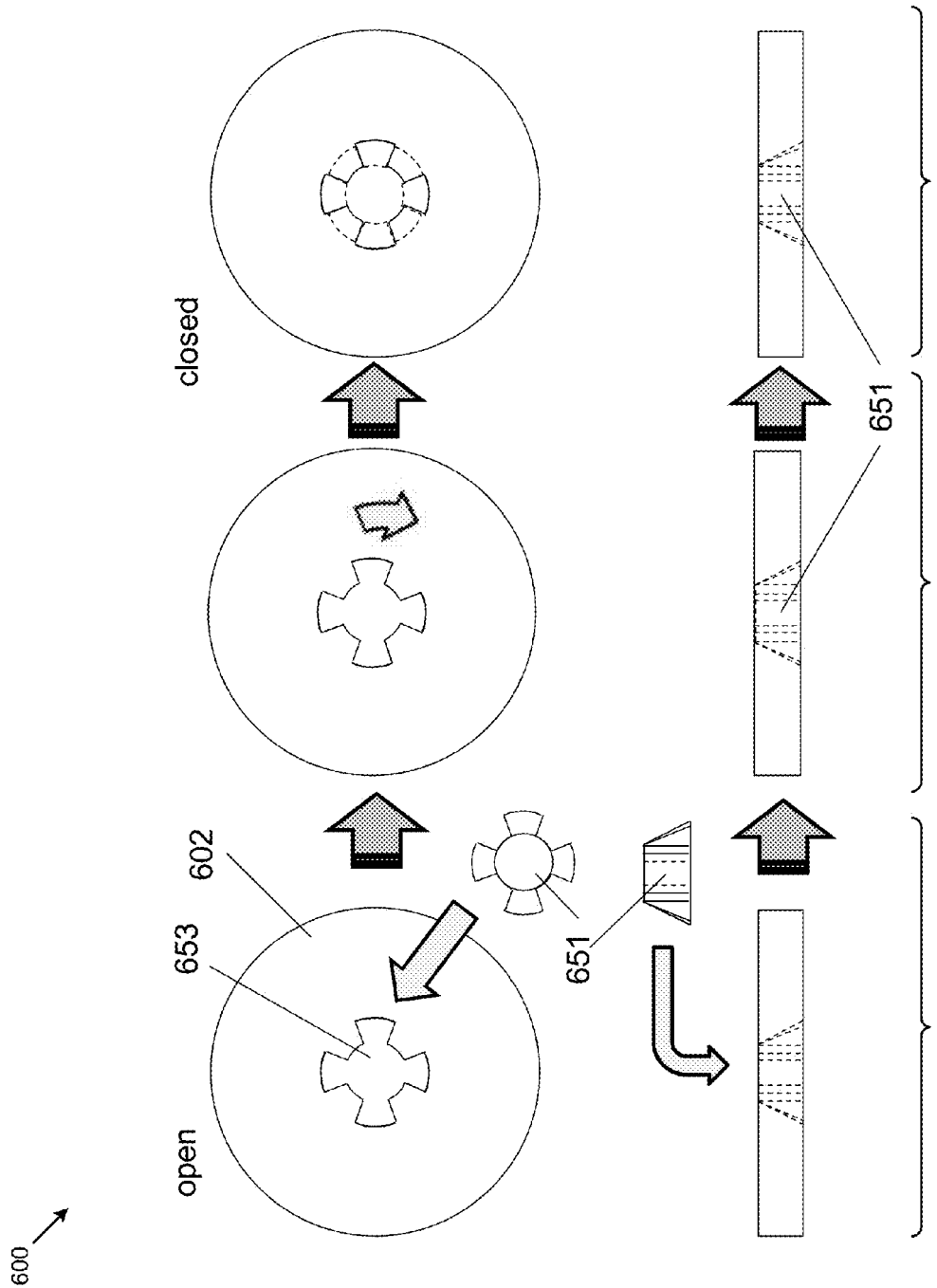
FIGS. 6A, 6B, and 6C are simplified diagrams of a crown insert apparatus configured as a fan/wedge structure, according to an embodiment of the present disclosure.

FIGS. 6A, 6B, and 6C are simplified diagrams of a crown insert apparatus 600 configured as a fan/wedge structure. This diagram is merely an illustration and should not unduly limit the scope of the claims herein. As shown, the fan/wedge structure includes features of both the fan and wedge embodiments.

In one specific embodiment, illustrated schematically in FIG. 6A, fan/wedge crown insert structure 651 is inserted through opening 653 in crown member 602, forming the configuration illustrated schematically in FIG. 6B. The fan/wedge crown insert structure 651 is then rotated, by approximately 45 degrees in the case illustrated, to provide a closed configuration as shown schematically in FIG. 6C. In the open configuration a capsule, a heater, or heating member and other components may be inserted into or removed from the high pressure apparatus. In the closed configuration the combination of the crown members, the crown inserts, and the tie rods are capable of supporting a large axial load.

Figure 7:
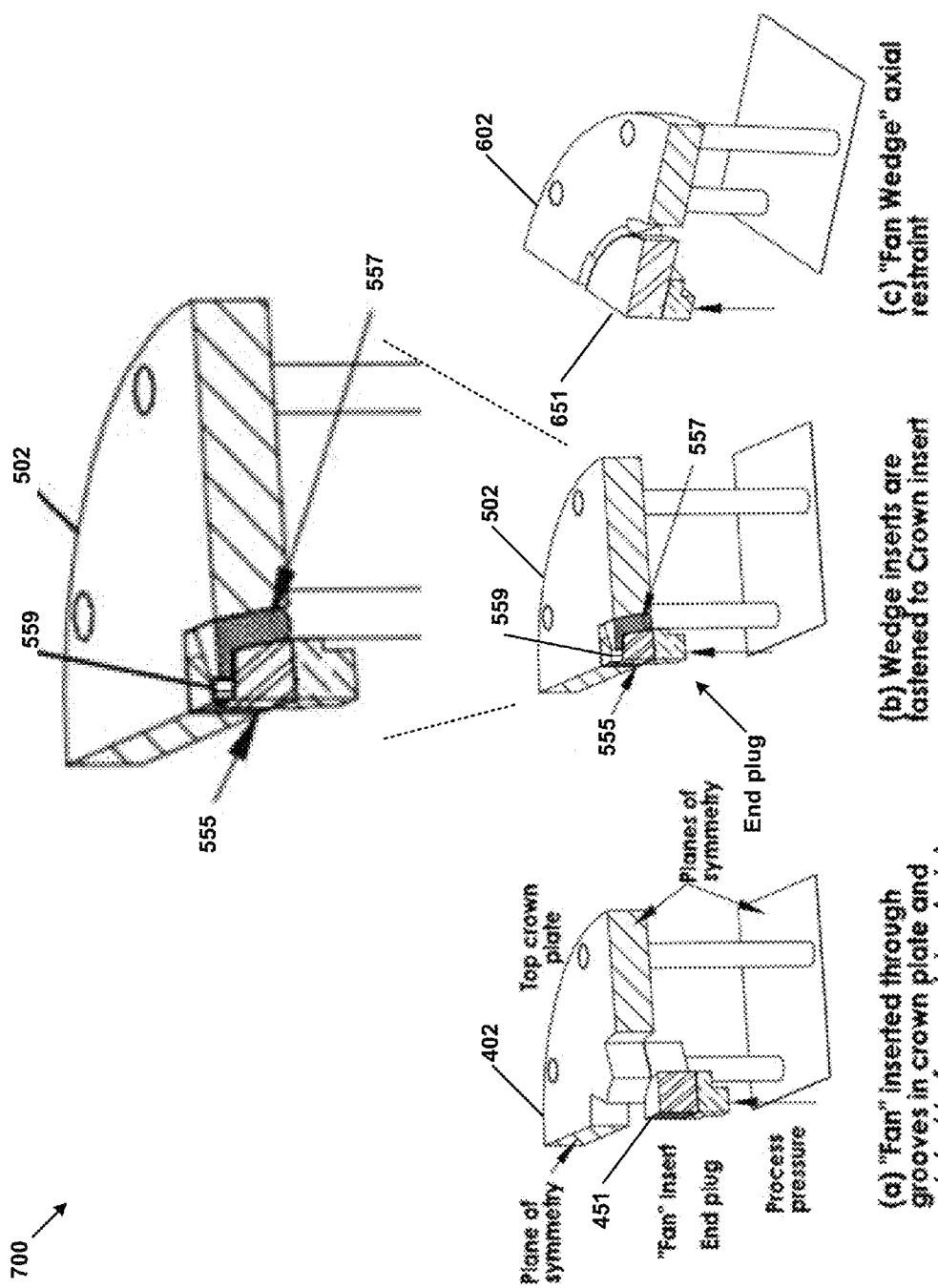
FIG. 7 is a simplified diagram showing three-dimensional views of the crown insert structures, according to embodiments of the present disclosure.

Three-dimensional views of these crown insert structures are described below, and shown in FIG. 7.

FIGS. 7A, 7B, and 7C are simplified diagrams showing three-dimensional views 700 of the crown insert structures. In each case the opening to the crown member is shown in the closed position. The insert can be rotated and removed in the case of the configurations shown in FIG. 7A and FIG. 7C. To open the configuration in FIG. 7B the components are removed successively, as described herein.

The apparatus is designed such that the resulting load path from the process pressure compresses the stack of radial restraint members thereby preventing the mating faces of the rings from separating during service. As a result the service life of the apparatus is considerably improved and maintenance related downtime is considerably reduced, (e.g., see FIG. 2A and FIG. 2B). The fraction of the axial load that is applied to compression of the radial restraint-stack may be controlled by adjusting the number or stiffness of tie rods connecting the top crown member to the bottom crown member in relation to the number or stiffness of tie rods connecting the crown members to the upper and lower restraint members.

The axial restraint at both top and bottom ends is provided using a "wedge" (e.g., see FIG. 5), "fan" (e.g., see FIG. 4) or "fan/wedge" (e.g., see FIG. 6) design that minimizes the number of fastening elements used thereby, considerably reducing the amount of time and effort needed to load and unload a reaction run.

A method according to a specific embodiment is briefly outlined below.

Provide an apparatus for high pressure crystal growth or material processing, such as the ones described above, but there can be others, the apparatus comprising a capsule region (for example, cylindrical in shape) surrounded by radial restraint structures and supported axially by tie rods coupled between crown plate and die restraint members, the opening regions to the capsule region through the crown plate members being closable by at least one of fan, wedge, or fan/wedge crown insert structures; Provide a capsule containing a solvent;

Place the capsule within an interior region of the capsule region and close the opening region to the capsule region by means of at least one of a fan, wedge, or fan/wedge crown insert structure;

Process the capsule with thermal energy to cause an increase in temperature within the capsule to greater than 200 degrees Celsius to cause the solvent to be superheated;

Form a crystalline material from a process of the superheated solvent;

Remove thermal energy from the capsule to cause a temperature of the capsule to change from a first temperature to a second temperature, which is lower than the first temperature;

Open an opening region to the capsule region of the high pressure apparatus by removing at least one of a fan, wedge, or fan/wedge crown insert structure;

Remove the capsule from the capsule region;

Open the capsule;

Remove the crystalline material; and

Perform other steps, as desired.

The above sequence of steps provides a method according to an embodiment of the present disclosure. In a specific embodiment, the present disclosure provides a method and resulting crystalline material provided by a high pressure apparatus having structured support members. Other alternatives can also be provided where steps are added, one or more steps are removed, or one or more steps are provided in a different sequence without departing from the scope of the claims herein. Details of the present method and structure can be found throughout the present specification and more particularly below.

Figure 8:
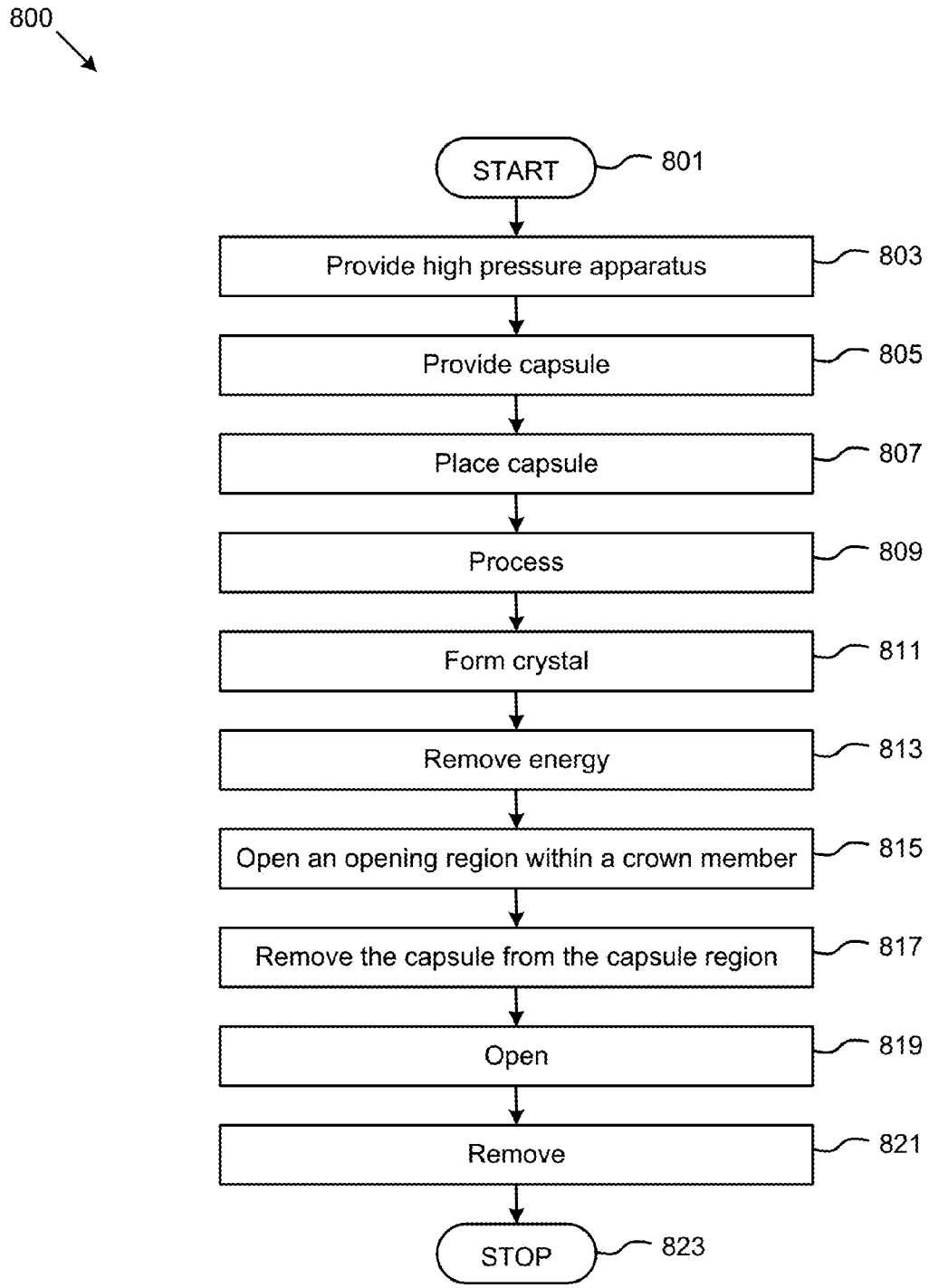
FIG. 8 is a simplified flow diagram of a method of processing a material within a supercritical fluid, according to an embodiment of the present disclosure.

FIG. 8 is a simplified flow diagram 800 of a method of processing a material within a supercritical fluid. This diagram is merely an example, which should not unduly limit the scope of the claims herein.

In a specific embodiment, the method begins with start, step 801. The method begins by providing an apparatus for high pressure crystal or material processing (see step 803), such as the one described above, but there can be others. In certain embodiments, the apparatus has a capsule region (for example, cylindrical in shape) surrounded by radial restraint structures and supported axially by tie rods coupled between crown plate and die restraint members. In certain embodiments, the opening regions to the capsule region through crown plate members are closable by at least one of fan, wedge, or fan/wedge crown insert structures.

In a specific embodiment, the method provides a capsule containing a solvent, such as ammonia (see step 805), for example. In a specific embodiment, the method places the capsule (see step 807) containing the solvent and starting crystal within an interior region of the capsule region. The method processes the capsule (see step 809) with thermal energy to cause an increase in temperature within the capsule to greater than 200 Degrees Celsius to cause the solvent to be superheated.

Referring again to FIG. 8, the method forms a crystalline material (see step 811) from a process of the superheated solvent. In certain embodiments, the crystalline material comprises a gallium-containing nitride crystal such as GaN, AlGaN, InGaN, and others. In a specific embodiment, the method removes thermal energy from the capsule (see step 813) to cause a temperature of the capsule to change from a first temperature to a second temperature, which is lower than the first temperature. Once the energy has been removed and temperature reduced to a suitable level, the method opens an opening region within a crown member (step 815), which mechanically held at least the capsule in place. In certain embodiments, the method removes the capsule from the capsule region (see step 817), free from the apparatus.

In a specific embodiment, the capsule is now free from the apparatus. In a specific embodiment, the capsule is opened, step 819. In a certain embodiment, the crystalline material is removed from an interior region of the capsule, step 821. Depending upon the embodiment, there can also be other steps, which can be inserted or added or certain steps can also be removed. In a specific embodiment, the method ends at stop, step 823.

The above sequence of steps provides a method according to an embodiment of the present disclosure. In a specific embodiment, the present disclosure provides a method and resulting crystalline material provided by a high pressure apparatus having structured support members. Other alternatives can also be provided where steps are added, one or more steps are removed, or one or more steps are provided in a different sequence without departing from the scope of the claims herein.

In certain embodiments, a gallium-containing nitride crystal or boule grown by methods such as those described above is sliced or sectioned to form wafers. The slicing, sectioning, or sawing may be performed by methods that are known in the art, such as internal diameter sawing, outer diameter sawing, fixed abrasive multiwire sawing, fixed abrasive multiblade sawing, multiblade slurry sawing, multiwire slurry sawing, ion implantation and layer separation, or the like. The wafers may be lapped, polished, and chemical-mechanically polished according to methods that are known in the art.

One or more active layers may be deposited on the well-crystallized gallium-containing nitride wafer. The active layer may be incorporated into an optoelectronic or electronic devices such as at least one of a light emitting diode, a laser diode, a photodetector, an avalanche photodiode, a transistor, a rectifier, and a thyristor; one of a transistor, a rectifier, a Schottky rectifier, a thyristor, a p-i-n diode, a metal-semiconductor-metal diode, high-electron mobility transistor, a metal semiconductor field effect transistor, a metal oxide field effect transistor, a power metal oxide semiconductor field effect transistor, a power metal insulator semiconductor field effect transistor, a bipolar junction transistor, a metal insulator field effect transistor, a heterojunction bipolar transistor, a power insulated gate bipolar transistor, a power vertical junction field effect transistor, a cascode switch, an inner sub-band emitter, a quantum well infrared photodetector, a quantum dot infrared photodetector, a solar cell, and a diode for photoelectrochemical water splitting and hydrogen generation.

Figure 9:
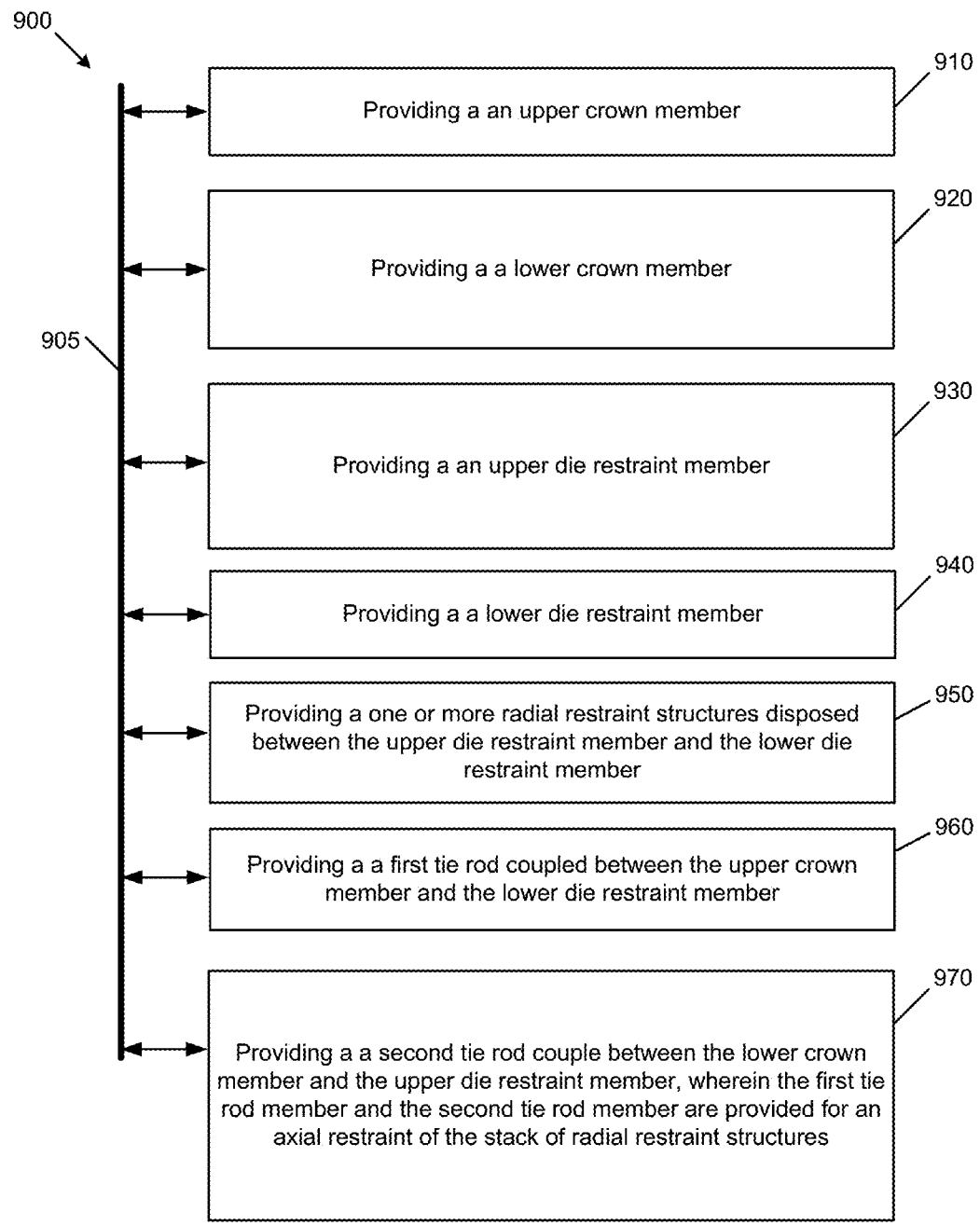
FIG. 9 is depicts a block diagram of a system to perform certain method steps for using an apparatus as disclosed herein.

FIG. 9 is depicts a block diagram of a system to perform certain method steps for using an apparatus as disclosed herein. As an option, the present system 900 may be implemented in the context of the architecture and functionality of the embodiments described herein. In some embodiments, system 900 comprises at least one processor and at least one memory (not shown), the memory serving to store program instructions corresponding to the operations of the system. An operation (e.g. implemented in whole or in part using program instructions) is connected to a communication link 905, and any module can communicate with other modules over communication link 905; any step of system 900 can be performed in a fully-automatic fashion, or in a semi-automatic fashion. Any method steps performed within system 900 may be performed in any order unless as may be specified in the claims. As shown, FIG. 9 implements an apparatus as a system 900, comprising one or more program instructions for: providing an upper crown member (see module 910); providing a lower crown member (see module 920); providing an upper die restraint member (see module 930); providing a lower die restraint member (see module 940); providing one or more radial restraint structures disposed between the upper die restraint providing member and the lower die restraint member (see module 950); providing a first tie rod coupled between the upper crown member and the lower die providing restraint member (see module 960); providing a second tie rod couple between the lower crown member and the upper die restraint member, wherein the first tie rod member and the second tie rod member are provided for an axial restraint of the stack of radial restraint structures (see module 970).

Figure 10:
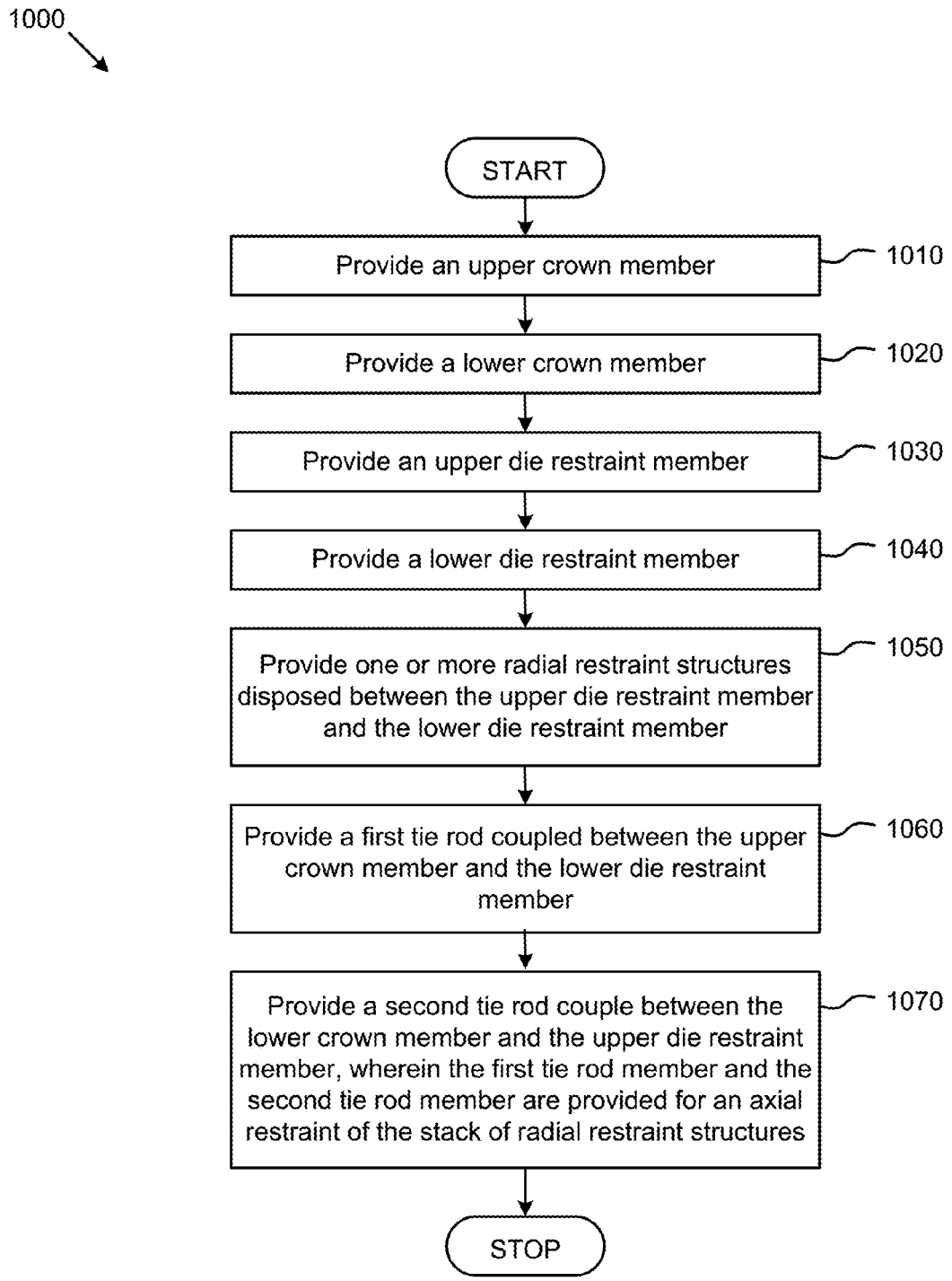
FIG. 10 depicts a method for processing material at elevated pressure, according to an embodiment of the present disclosure.

FIG. 10 depicts a method for processing material at elevated pressure, the method comprising:

providing an upper crown member (see step 1010);

providing a lower crown member (see step 1020);

providing an upper die restraint member (see step 1030);

providing a lower die restraint member (see step 1040);

providing one or more radial restraint structures disposed between the upper die restraint member and the lower die restraint member (see step 1050);

providing a first tie rod coupled between the upper crown member and the lower die restraint member (see step 1060); and providing a second tie rod couple between the lower crown member and the upper die restraint member, wherein the first tie rod member and the second tie rod member are provided for an axial restraint of the stack of radial restraint structures (see step 1070).

While the above is a full description of the specific embodiments, various modifications and alternative constructions and equivalents may be used. Therefore, the above description and illustrations should not be taken as limiting the scope of the present disclosure which is defined by the appended claims.

What is claimed is:

1. An apparatus for processing material at elevated pressure, the apparatus comprising:
    an upper crown member;
    a lower crown member;
    an upper die restraint member;
    a lower die restraint member, said upper and lower die restraint members being disposed between said upper and lower crown members;
    one or more radial restraint structures disposed between the upper die restraint member and the lower die restraint member, said radial restraint structures defining an interior region configured to receive a processing chamber, said radial restraint structures being configured to resist an outward radial force as a result of pressure in said processing chamber, said upper and lower crown members being disposed axially on either end of said interior region and configured to resist an outward axial force as a result of pressure in said processing chamber;
    one or more first connecting members coupling the upper crown member and the lower die restraint member; and one or more second connecting members coupling the lower crown member and the upper die restraint member, wherein the first and second connecting members are configured for an axial restraint of the stack of radial restraint structures by transferring at least a portion of an outward axial force applied to said upper and lower crown members as a result of pressure in said processing chamber to said first and second connecting members, thereby compressively loading said radial restraint structures between said upper and lower die restraint members.

2. The apparatus of claim 1, further comprising one or more third connecting members coupling the upper crown member and the upper crown member.

3. The apparatus of claim 1, further comprising said a processing chamber disposed within said interior region.

4. The apparatus of claim 3, wherein a heater is disposed between the processing chamber and the one or more radial restraint structures.

5. The apparatus of claim 1, wherein the at least one radial restraint structures comprises a stack of two or more ring assemblies, the two or more ring assemblies comprising a high strength enclosure ring and a ceramic ring or ceramic radial segment assembly.

6. An apparatus for growing a gallium and nitrogen containing material, the apparatus comprising:
a first crown plate structure comprising an opening region, the opening region comprising a first pattern configured to insert a capsule device there through;
a second crown plate structure operably coupled to the first crown plate structure to maintain a processing region between the first crown plate structure and the second crown plate structure, the processing region configured to house a capsule device; and
a crown insert structure configured to plug the opening region, the crown insert structure comprising a second pattern complementary with the first pattern, the second pattern configured to be insertable into the first pattern for plugging the opening region when the crown insert structure is moved in a direction normal to the first crown structure; and the second pattern configured to be off-set from the first pattern when rotated in a predetermined manner while the crown insert is engaged with the first pattern in the opening region such that the crown insert is substantially held in place with the first crown plate structure to plug the opening region and support an axial load.

7. The apparatus of claim 6, wherein the first pattern comprises a first pair of opposing extension regions and the second pattern comprises a second pair of opposing extension regions.

8. The apparatus of claim 6, wherein the first pattern comprises a plurality of first extension regions and the second pattern comprises a plurality of second extension regions.

9. The apparatus of claim 6, wherein each of the first crown plate structure the second crown plate structure, and the crown insert structure comprise a material independently selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, and cobalt and its alloys or superalloys.

10. The apparatus of claim 6, wherein an angle between a normal to planes of contact between the first pattern and the second pattern and a normal to the first crown plate structure lies between about 5 degrees and about 60 degrees.

11. The apparatus of claim 6, wherein the axial load is greater than about 500 tons.

12. An apparatus for growth of a gallium and nitrogen containing material, the apparatus comprising:
a first crown plate structure comprising an opening region, the opening region comprising a first pattern configured to insert a capsule device there through, the first pattern comprising a first open region in communication with a second open region, the second open region being larger than the first open region;
a second crown plate structure operably coupled to the first crown structure to maintain a processing region between the first crown plate structure and the second crown plate structure, the processing region being capable of housing a capsule device; and
a crown insert device configured to plug the opening region, the crown insert device comprising a plug member, a plurality of locking members, and at least one key member, the plurality of locking members being configured with the key member to hold the plug member within a vicinity of the opening region to plug the opening region with the crown insert device and support an axial load.

13. The apparatus of claim 12, wherein the plug member is configured as a truncated pyramid shape.

14. The apparatus of claim 12, wherein each of the plurality of locking members is configured as a sleeve to be disposed between a portion of the plug member and the first pattern.

15. The apparatus of claim 12, wherein the at least one key member comprises a square shape or a rectangular shape.

16. The apparatus of claim 12, wherein each of the first crown plate structure, the crown insert structure, and the second crown structure comprise a material independently selected from steel, low-carbon steel, SA723 steel, SA266 carbon steel, 4340 steel, A-286 steel, iron based superalloy, 304 stainless steel, 310 stainless steel, 316 stainless steel, 340 stainless steel, 410 stainless steel, 17-4 precipitation hardened stainless steel, nickel and its alloys or superalloys, and cobalt and its alloys or superalloys.

17. The apparatus of claim 12, wherein the angle between the normal to the planes of contact between the plug member and the locking members and the normal to the first crown plate structure lies between about 5 degrees and about 60 degrees.

18. The apparatus of claim 12, wherein the axial load is greater than about 500 tons.

19. The apparatus of claim 1, wherein said first and second connecting members are tie rods.

20. The apparatus of claim 1, wherein at least one of said first and second die restraint members does not provide radial restraint.

21. The apparatus of claim 1, further comprising first and second plugs between said processing chamber and said upper and lower crown members.

22. The apparatus of claim 2, wherein a portion of said outward axial force applied to said upper and lower crown members is transferred to said third connection members.

* * * * *

UNITED STATES PATENT AND TRADEMARK OFFICE
CERTIFICATE OF CORRECTION

PATENT NO. : 9,724,666 B1  
APPLICATION NO. : 13/656615  
DATED : August 8, 2017  
INVENTOR(S) : Pakalapati Tirumala Rajeev, Douglas W. Pocius and Mark P. D'Evelyn Page 1 of 1

It is certified that error appears in the above-identified patent and that said Letters Patent is hereby corrected as shown below:

On the Title Page

Item (72) In the First Named Inventor, reverse his first name and last name from "Pakalapati Tirumala Rajeev" to "Rajeev Tirumala Pakalapati."

In the Claims

In Claim 3, replace ""... comprising said a" with "... comprising said."

Signed and Sealed this  
Ninth Day of April, 2019

Andrei Iancu  
*Director of the United States Patent and Trademark Office*